(12) United States Patent
Gusyatin

(10) Patent No.: US 11,940,757 B2
(45) Date of Patent: Mar. 26, 2024

(54) LENS-FREE HOLOGRAPHIC OPTICAL SYSTEM FOR HIGH SENSITIVITY LABEL-FREE MICROBIAL GROWTH DETECTION AND QUANTIFICATION FOR SCREENING, IDENTIFICATION, AND SUSCEPTIBILITY TESTING

(71) Applicant: Accelerate Diagnostics, Inc., Tucson, AZ (US)

(72) Inventor: Oleg Gusyatin, Tucson, AZ (US)

(73) Assignee: Accelerate Diagnostics, Inc., Tucson, AZ (US)

( * ) Notice: Subject to any disclaimer, the term of this patent is extended or adjusted under 35 U.S.C. 154(b) by 223 days.

(21) Appl. No.: 17/353,943

(22) Filed: Jun. 22, 2021

(65) Prior Publication Data
US 2022/0011722 A1  Jan. 13, 2022

Related U.S. Application Data

(63) Continuation of application No. 16/028,287, filed on Jul. 5, 2018, now Pat. No. 11,079,719.
(Continued)

(51) Int. Cl.
| | |
|---|---|
| *G03H 1/10* | (2006.01) |
| *C12M 1/34* | (2006.01) |
| *G01N 15/02* | (2006.01) |
| *G01N 15/0227* | (2024.01) |
| *G01N 15/10* | (2006.01) |

(Continued)

(52) U.S. Cl.
CPC .............. *G03H 1/10* (2013.01); *C12M 41/36* (2013.01); *G01N 15/0227* (2013.01); *G01N 15/1434* (2013.01); *G01N 15/1475* (2013.01); *G01N 23/20* (2013.01); *G02B 21/0008* (2013.01); *G02B 21/365* (2013.01); *G03H 1/0443* (2013.01); *G01N 2015/0233* (2013.01); *G01N 2015/1006* (2013.01); *G01N 2015/1454* (2013.01); *G01N 2015/1493* (2013.01); *G01N 2015/1497* (2013.01); *G03H 2001/0033* (2013.01); *G03H 2001/0447* (2013.01); *G03H 1/0866* (2013.01); *G03H 2001/2655* (2013.01); *G03H 2222/13* (2013.01); *G03H 2222/52* (2013.01); *G03H 2226/13* (2013.01); *G03H 2227/03* (2013.01)

(58) Field of Classification Search
None
See application file for complete search history.

(56) References Cited

U.S. PATENT DOCUMENTS

2016/0289729 A1* 10/2016 Richards ................ C12Q 1/025

\* cited by examiner

*Primary Examiner* — Stephone B Allen
*Assistant Examiner* — Tamara Y. Washington
(74) *Attorney, Agent, or Firm* — Wood Herron & Evans LLP

(57) ABSTRACT

Disclosed are optical interrogation apparatus that can produce lens-free images using an optoelectronic sensor array to generate a holographic image of sample objects, such as microorganisms in a sample. Also disclosed are methods of detecting and/or identifying microorganisms in a biological sample, such as microorganisms present in low levels. Also disclosed are methods of using systems to detect microorganisms in a biological sample, such as microorganisms present in low levels. In addition or as an alternative, the methods of using systems may identify microorganisms present in a sample and/or determine antimicrobial susceptibility of such microorganisms.

11 Claims, 17 Drawing Sheets

Related U.S. Application Data

(60) Provisional application No. 62/528,825, filed on Jul. 5, 2017.

(51) Int. Cl.
    *G01N 15/14*     (2006.01)
    *G01N 15/1434*     (2024.01)
    *G01N 23/20*     (2018.01)
    *G02B 21/00*     (2006.01)
    *G02B 21/36*     (2006.01)
    *G03H 1/00*     (2006.01)
    *G03H 1/04*     (2006.01)
    *G03H 1/08*     (2006.01)
    *G03H 1/26*     (2006.01)

LENS-FREE HOLOGRAPHIC OPTICAL SYSTEM FOR HIGH SENSITIVITY LABEL-FREE MICROBIAL GROWTH DETECTION AND QUANTIFICATION FOR SCREENING, IDENTIFICATION, AND SUSCEPTIBILITY TESTING

CROSS REFERENCE TO RELATED APPLICATION

This application is a continuation of, and claims priority to, U.S. patent application Ser. No. 16/028,287; which claims the benefit of U.S. Provisional Patent Application No. 62/528,825, filed Jul. 5, 2017, the disclosures of which are hereby incorporated by reference in their entirety.

FIELD

The present disclosure relates to microorganism detection.

BACKGROUND

Microbial infections are best treated as early as possible to confer the greatest opportunity for patient recovery and to limit morbidity and mortality. For example, roughly 85% of patients demonstrating symptoms of infection will not have sufficient microorganism concentrations in their blood at initial presentation to enable detection of the causative agent. Corresponding blood samples may appear negative for microorganisms until many doubling events occur, at which point sufficient numbers of microbial cells will be present and reach the lower threshold of standard detection testing.

Automated microscopy systems traditionally used to detect microbial cells in patient samples comprise various configurations of sample containers, reaction reservoirs, reagents, and optical detection systems. Such optical detection systems are generally configured to obtain images via, for example, dark field and fluorescence photomicrographs of microorganisms contained in reaction reservoirs, such as flowcells (e.g., microfluidic channels/chamber, perfusion chambers, and the like). Such optical detection systems also comprise a controller configured to direct operation of the system and process microorganism information derived from photomicrographs. These systems generally are not capable of detecting extremely low concentrations of microorganisms in direct from patient samples, and require a culturing period to ensure that if present, viable microbial cells reach a detectable level to statistically ensure that a negative detection reading is truly negative.

A phenotypical approach to detection of viable microbial population in a sample involves in vivo monitoring of microbial growth. While many approaches have been proposed to achieve this (impedance, weight, growth by-product concentration monitoring, etc.), solutions based on direct optical interrogation remain elusive as an alternative. Optical approaches are typically constrained by factors such as optical resolution as well as the need for timely acquisition of microbial division (growth) over time (time-lapse microscopy). Detection of small concentrations of viable bacteria (typically $<<10^5$ cfu/mL) presents additional challenges as it requires large volumes of direct from patient sample to be interrogated (on the order of milliliters) to ensure a high probability of detection. Moreover, achieving better sensitivity in time-to-detection, such large volumes need to be scanned at rates higher than bacterial division rates.

Usually, optical interrogation at high resolution relies on lengthy multiple pass scanning methodologies employing high precision 3-D stages, high quality objectives, and fine focusing techniques. Moreover, label-free (unstained) bacteria require the employment of less common imaging modes—such as phase contrast or differential contrast interference microscopy—due to a very small difference in refractive index with suspension media. As a result, hardware and software requirements for such applications scale poorly with sample volume under examination.

SUMMARY

To address this problem of detecting the presence of microbial cells in low concentrations in patient samples, an imaging system was devised, which uses a three-dimensional ("3D") or four-dimensional ("4D") holographic approach. For example, images of a patient sample in a volume (3D) can be obtained over time (4D), for example using video frame rates. Unlike conventional imaging techniques, the instant holographic imaging system does not rely on multiple focal planes of cells growing in a location requiring repeated image capturing over time. Instead, a matrix array of optoelectronic sensors is employed to obtain a plethora of single images captured per time point from a 3D or 4D suspension of microorganisms in a medium whose properties physically retain microorganisms in a single location. As those microorganisms divide, their offspring remain in the same location of their mother cells, eliminating the need to track individual cell movement across a large volume of sample. The focal point is numerically determined after the holographic image is captured. The process permits simultaneous imaging of a large volume of patient sample to improve the chances of detecting viable microorganisms present in low concentrations.

Provided herein is a system that includes a holographic optical apparatus situated to determine the presence of a microorganism immobilized in a sample volume based on a detected variation over time of a hologram of the sample volume, such as a detected variation corresponding to four or fewer microorganism doubling events, or three or fewer microorganism doubling events. In some examples, the holographic apparatus is an in-line holographic apparatus, and the hologram is an in-line hologram. In some examples, the in-line holographic optical apparatus includes a reference beam source situated to direct a reference beam to the sample volume; a sample receptacle situated to hold the sample volume in view of the reference beam; an optical sensor (such as a complementary metal oxide semiconductor (CMOS) sensor having a pixel pitch of 1.5 µm or smaller) situated to detect the in-line hologram formed by the reference beam and the sample volume; and a controller coupled to the optical sensor and configured to determine the variation over time of the in-line hologram. In some examples, the optical sensor has a pixel pitch of 1 µm/pixel or smaller and the controller is configured to determine, based on the detected in-line hologram, morphological characteristics of the microorganism determined to be present. The reference beam source can include a pinhole aperture situated to receive multi-wavelength illumination from an illumination source and the reference beam is directed lens-free from the pinhole aperture to the sample volume and optical sensor. In some examples, the reference beam source is situated to direct a plurality of reference beams to the sample volume and to adjacent portions of the optical sensor so as to mosaic the field of view of the in-line holographic apparatus, for example, wherein the adjacent portions of the optical sensor portions correspond to separate CMOS sensors. In some examples, the multi-wavelength illumination received by the illumination source is incoherent and the reference beam comprises incoherent illumination. In some examples, the controller is configured to reconstruct the spatial characteristics of the sample volume based on the detected in-line hologram, diffraction propagation approximation, and a phase retrieval algorithm. In some examples, the controller is configured to determine a focal plane of the microorganism immobilized in the sample volume. In some examples, the sample volume includes at least one sample reaction chamber situated as a growth control with a first sample portion situated in the absence of an antimicrobial agent, and at least one sample reaction chamber situated as an antimicrobial susceptibility test with a second sample portion situated in the presence of an antimicrobial agent. The sample volume can include a plurality of growth channels having selective media. In some examples, the holographic apparatus is situated to determine the presence based on the detected variation with the sample volume having a microorganism concentration of 100 CFU/mL or less, such as 10 CFU/mL or less. In some examples, the holographic apparatus is situated to display a time-lapse image associated with the sample volume at a time-resolution that is faster than a microorganism division rate. In some examples, the time-lapse image corresponds to one or more of the hologram and one or more planes of the sample volume.

Also provided are methods for detecting a microorganism in a sample (and in some examples also identifying the microorganism, determining the antimicrobial susceptibility of the microorganism, or both), which can use the disclosed systems (such as those that utilize holography). In some examples, the sample is a polymicrobial sample. In some examples, the biological sample comprises 100 CFU/mL or less, such as 10 CFU/mL or less, of the microorganism. In some examples, the microorganism comprises bacteria, protozoa, fungi, or combinations thereof. In some examples, the method includes detecting an in-line hologram of a suspended biological sample (such as a blood, urine, respiratory, or saliva sample); and for at least one immobilized object in the suspended biological sample, determining a variation over time of the in-line hologram that is associated with an indication that the at least one immobilized object is a microorganism in the biological sample. In some examples, determining a variation over time includes determining a spatial difference over time associated with the at least one immobilized object and corresponding to a microorganism growth or decline. In some examples, the suspended biological sample is suspended in a porous medium, and the method further includes incubating the suspended biological sample in an environment conducive to microorganism replication (e.g., growth, division, or both). In some examples, the method further includes interrogating the suspended biological sample in an optical interrogation system; wherein the optical interrogation system includes at least one optical sensor situated to perform the detecting of the in-line hologram. In some examples, the method further includes determining a focal plane corresponding to a plane of highest variance in the suspended biological sample that is associated with the at least one immobilized object. In some examples, the method further includes reconstructing spatial characteristics of the suspended biological sample based on the detected in-line hologram and a numerical reconstruction algorithm. In some examples, the optical sensor has a pixel pitch of 1 µm/pixel or smaller and the method further includes determining, based on the detected in-line hologram, morphological characteristics of the at least one object corresponding to a microorganism. In some examples, the method further includes directing a plurality of reference beams to the suspended biological sample and to adjacent portions of the optical sensor so as to mosaic the field of view of the optical interrogation system. In some examples, the suspended biological sample includes at least one sample reaction chamber situated as a growth control with a first sample portion situated in the absence of an antimicrobial agent, and at least one sample reaction chamber situated as an antimicrobial susceptibility test (AST) with a second sample portion situated in the presence of at least one antimicrobial agent. An exemplary growth control includes Mueller-Hinton agar (MHA). Exemplary antimicrobial agents include one or more of amikacin, ampicillin, ampicillin-sulbactam, aztreonam, cefazolin, cefepime, ceftaroline, ceftazidime, ceftriaxone, ciprofloxacin, colistin, daptomycin, doxycycline, erythromycin, ertapenem, gentamicin, imipenem, linezolid, meropenem, minocycline, piperacillin-tazobactam, tobramycin, trimethoprim-sulfamethoxazole, and vancomycin. The suspended biological sample can be present in a plurality of flowcells, each comprising selective and differential media, such as blood agar, Eosin Methylene Blue (EMB) agar, mannitol salt agar, MacConkey agar, phenylethyl alcohol (PEA) agar, and YM agar, by way of example and not limitation. In some examples, the method further includes displaying a time-lapse image associated with the suspended biological sample at a time-resolution that is faster than a microorganism division or multiplication rate (e.g., the rate at which a bacterium or yeast divides into two daughter cells, the rate at which a protist divides itself into two or more daughter cells). In some examples, the time-lapse image corresponds to one or more of the detected in-line hologram and one or more planes of the suspended biological sample.

In some examples, the methods include detecting a variation of an in-line hologram over time of a biological sample; and determining the presence of a microorganism immobilized in the biological sample based on the detected variation.

In some examples, the methods include detecting an in-line hologram of an immobilized biological sample at a first time and a second time; comparing the in-line holograms to determine a hologram variation associated with a microorganism; and determining whether a microorganism is present in the biological sample based on the variation.

In some examples, the system includes at least one processor, and one or more computer-readable storage media including stored instructions that, responsive to execution by the at least one processor, cause the system to compare a first in-line hologram of a sample volume at a first time and a second in-line hologram of the sample volume at a second time and to determine a hologram variation between the first in-line hologram and second in-line hologram that is associated with an indication as to the presence of a microorganism immobilized in the sample volume.

In particular sequences of using holographic optical apparatus and methods examples herein, screening can be performed to determine the presence of a microorganism, AST can be performed, and then identification.

Also provided are optical interrogation platform systems. In some examples, such a system includes an in-line holographic setup comprising a single-aperture multi-wavelength illumination; and a complementary metal oxide semiconductor (CMOS) sensor having a pixel pitch selected so as to detect a holographic variation over time associated with the presence of an immobilized microorganism in a sample volume.

Also provided are automated methods of lens-free microscopy for detecting one or more microorganisms in a sample (and in some examples also identifying the microorganism, determining the antimicrobial susceptibility of the microorganism, or both). In some examples, the methods include suspending a biological sample in a porous medium; introducing the suspended biological sample to a sample reaction chamber; subjecting the porous medium to a phase change to immobilize microorganism cells in the suspended biological sample in three-dimensional space; incubating the suspended biological sample in an environment conducive to microorganism replication; interrogating the suspended biological sample in an automated optical interrogation system using one or more optoelectronic sensors to locate the optimal focal plane for each microorganism in the sample; tracking spatial differences to detect changes in growth of microorganisms over time; and acquiring holographic images of replicating microorganisms, thereby detecting their presence in the biological sample. In some examples, the phase change produces a gelled medium. In some examples, the microorganisms are present in the biological sample at a concentration of approximately $10^2$ bacteria per 1 mL or $10^2$ bacteria per 300 uL of sample.

According to another aspect of the disclosed technology, systems can be automated and include an automated holographic optical apparatus situated to determine at least the antimicrobial susceptibility of a microorganism corresponding to an object in a sample volume based on a detected variation over time of a hologram of the sample volume, an output of at least one deeply supervised convolutional neural network, and a phenotypical behavior of the microorganism, wherein the phenotypical behavior of the microorganism is classified based on the detected variation and the output of the at least one deeply supervised convolutional neural network. In representative systems, the holographic apparatus is an in-line holographic apparatus and the hologram is an in-line hologram, and the in-line holographic optical apparatus includes a reference beam source situated to direct a reference beam to the sample volume, a sample receptacle situated to hold the sample volume in view of the reference beam, an optical sensor situated to detect the in-line hologram formed by the reference beam and the sample volume, and a controller coupled to the optical sensor and that includes at least one processor and one or more computer-readable storage media including stored instructions that, responsive to execution by the at least one processor, cause the controller to determine the variation over time of the in-line hologram. In some examples, the controller is configured to reconstruct the spatial characteristics of the sample volume based on the detected in-line hologram, diffraction propagation approximation, and a phase retrieval algorithm. In further examples, the controller is configured to determine a focal plane of the microorganism in the sample volume based on the reconstructed spatial characteristics. In particular examples, the at least one deeply supervised convolutional neural network includes a spatial reconstruction deeply supervised convolutional neural network configured to produce an output corresponding to a reconstruction of the spatial characteristics of the sample volume based on a trained set of network layers, and wherein the controller is configured to reconstruct the spatial characteristics of the sample volume using the reconstruction deeply supervised convolutional neural network. In selected examples, the at least one deeply supervised convolutional neural network includes a microorganism identification deeply supervised convolutional neural network configured to produce an output corresponding to a microorganism identification, microorganism morphology identification, microorganism movement identification, and/or microorganism phenotypic classification for the microorganism in the sample volume based on a trained set of network layers, and wherein the controller is configured to identify the microorganism, microorganism morphology, microorganism movement, and/or classify the microorganism phenotypical behavior using the microorganism identification deeply supervised convolutional neural network. In some examples, the controller is configured to determine a 3D position and/or morphological characteristics of the microorganism based on the in-line hologram. In further embodiments, the controller is configured to associate the object detected in a later hologram with the object detected in an earlier hologram, based on proximity or morphological characteristics of the objects detected from the variation over time of the in-line hologram. In particular examples, the controller is configured to form an object track for the object in the sample volume based on the detected variation over time of the in-line hologram. In some embodiments, the controller is configured to identify the object as the microorganism in the sample volume based on the detected variation over time of the in-line hologram. In some embodiments, the controller is configured to classify a phenotypical behavior of the microorganism in the sample volume based on the detected in-line hologram. In some examples classifying a phenotypical behavior, the controller is configured to determine a correspondence between the phenotypic behavior of the microorganism and presence, concentration, and taxon of the microorganism in the sample volume. In further examples classifying a phenotypical behavior, the sample volume includes a plurality of sample volume portions situated in a respective at least one growth control, at least one selective media, and at least one antimicrobial flow cell that are held by the sample receptacle, and the controller is configured to determine the presence, taxon, and an antibiogram of the microorganism or multiple microorganisms based on the at least one growth control, the at least one selective media, and the at least one anti-microbial flow cell. In some embodiments with an optical sensor, the optical sensor is a complementary metal oxide semiconductor (CMOS) sensor having a pixel pitch of 1.5 μm or smaller. In further embodiments with an optical sensor, the optical sensor has a pixel pitch of 1 μm/pixel or smaller and the controller is configured to determine, based on the detected in-line hologram, morphological characteristics of the microorganism. In some embodiments, the reference beam source includes a plurality of pinhole apertures spaced apart from each other by 1 mm or less with each of the pinhole apertures configured to emit respective reference subbeams at different respective wavelengths. In further embodiments, the reference beam source includes a pinhole aperture situated to receive illumination from an illumination source and the reference beam source is configured to direct the reference beam lens-free from the pinhole aperture to the sample volume and optical sensor. In some pinhole aperture examples, the illumination source is configured to generate illumination at multiple wavelengths. In further pinhole aperture examples, the illumination received from the illumination source by the pinhole aperture is incoherent and the reference beam comprises incoherent illumination. In some embodiments, the reference beam source is situated to direct a plurality of reference beams to the sample volume and to adjacent portions of the optical sensor so as to mosaic the field of view of the in-line holographic apparatus. In some mosaic examples, the adjacent portions of the optical sensor correspond to separate CMOS sensors. In further examples, the sample volume includes a plurality of sample volume portions, including a first sample volume portion situated in a first sample reaction chamber that is held by the sample receptacle, wherein the first sample volume portion is situated as a growth control volume by having an absence of an antimicrobial agent, and including a second sample volume portion situated in a second sample reaction chamber, wherein the second volume portion is situated as an antimicrobial susceptibility test volume in the presence of a predetermined antimicrobial agent. In particular examples, the sample reaction chambers include a plurality of growth channels having selective media. In some embodiments, the holographic apparatus is situated to determine a presence of the microorganism based on the detected variation with the sample volume having a microorganism concentration of 10 cfu/mL or less. In further embodiments, the holographic apparatus is situated to display a time-lapse image associated with the sample volume at a time-resolution that is faster than a microorganism division rate. In some time-lapse examples, the time-lapse image corresponds to one or more of the hologram and one or more planes of the sample volume. In some embodiments, a time period of the detected variation corresponds to four or fewer microorganism doubling events. In further embodiments, a time period of the detected variation corresponds to three or fewer microorganism doubling events. In representative systems, the microorganism is immobilized in the sample volume.

According to a further aspect of the disclosed technology, methods includes detecting an in-line hologram of a suspended biological sample, measuring for at least one microorganism in the suspended biological sample, a variation over time of the in-line hologram, and determining the presence or absence of antimicrobial susceptibility for the at least one microorganism in the suspended biological sample based on the measured variation over time of the in-line hologram of the suspended biological sample, an output of at least one deeply supervised convolutional neural network associated with the measured hologram, and a phenotypical behavior of the at least one microorganism, wherein the phenotypical behavior is classified based on the detected variation and the output of the at least one deeply supervised convolutional neural network. In some examples, the at least one microorganism is immobilized in the suspended biological sample. Some embodiments can include, before determining presence or absence of antimicrobial susceptibility, determining whether a microorganism is present in the suspended biological sample based on the measured variation over time of the in-line hologram. Particular examples include suspending a biological sample in a porous medium to form the suspended biological sample, introducing the suspended biological sample to a sample reaction chamber, subjecting the porous medium to a phase change to immobilize the at least one microorganism in the suspended biological sample in three-dimensional space, incubating the suspended biological sample in an environment conducive to microorganism replication, wherein detecting the in-line hologram and determining the variation over time includes interrogating the suspended biological sample in an automated optical interrogation system using one or more optoelectronic sensors to locate an optimal focal plane for each of the immobilized microorganisms in the biological sample, tracking spatial differences to detect changes in growth of the at least one immobilized microorganism over time, and acquiring holographic images of the replicating at least one microorganism, thereby detecting its presence in the biological sample. In some examples, the phase change produces a gelled medium. In further examples, the at least one microorganism is present in the biological sample at a concentration of approximately $10^2$ bacteria per 1 mL of sample. In some examples, the at least one microorganism is immobilized, and the determining a variation over time includes determining a spatial difference over time associated with the at least one immobilized microorganism and corresponding to a microorganism growth or decline. In selected examples, the at least one deeply supervised convolutional neural network includes a spatial reconstruction deeply supervised convolutional neural network configured to produce an output corresponding to a reconstruction of the spatial characteristics of the suspended biological volume based on a trained set of network layers. In additional examples, the at least one deeply supervised convolutional neural network includes a microorganism identification deeply supervised convolutional neural network configured to produce an output corresponding to a microorganism identification, microorganism morphology identification, microorganism movement identification, and/or microorganism phenotypic classification for the at least one microorganism in the suspended biological sample based on a trained set of network layers. In examples, the sample material of the suspended biological sample is suspended in a porous medium, and the suspended biological sample is incubated in an environment conducive to microorganism replication. In representative embodiments, the in-line hologram is detected with an optical sensor comprising one or more sensor portions. In selected examples, each of the optical sensor portions includes a plurality of pixels with a pixel pitch of 1 µm/pixel or smaller. Some examples can include directing a plurality of reference beams to the suspended biological sample and to adjacent portions of the optical sensor corresponding to the respective optical sensor portions to produce a mosaicked field of view of the in-line hologram. Some embodiments include determining a focal plane corresponding to a plane of highest variance in the suspended biological sample that is associated with the at least one object. Additional examples include reconstructing spatial characteristics of the suspended biological sample based on the detected in-line hologram and a numerical reconstruction algorithm. In some embodiments, the suspended biological sample is supported by a sample receptacle of an in-line holography apparatus situated to perform the detecting, measuring, and determining, and wherein a first sample portion of the suspended biological sample is located in a first sample reaction chamber in the absence of an antimicrobial agent so as to correspond to a growth control, and wherein a second sample portion of the suspended biological sample is located in a second sample reaction chamber in the presence of at least one antimicrobial agent. In some examples, growth control comprises Mueller-Hinton agar (MHA). In selected examples, the at least one antimicrobial agent comprises amikacin, ampicillin, ampicillin-sulbactam, aztreonam, cefazolin, cefepime, ceftaroline, ceftazidime, ceftriaxone, ciprofloxacin, colistin, daptomycin, doxycycline, erythromycin, ertapenem, gentamicin, imipenem, linezolid, meropenem, minocycline, piperacillin-tazobactam, tobramycin, trimethoprim-sulfamethoxazole, vancomycin, or combinations thereof. In some embodiments, suspended biological sample includes sample volume portions that are present in a plurality of respective flowcells comprising selective and differential media. In particular examples, the selective and differential media comprise blood agar, Eosin Methylene Blue (EMB) agar, mannitol salt agar, MacConkey agar, phenylethyl alcohol (PEA) agar, or YM agar. Some embodiments can include displaying a time-lapse image associated with the suspended biological sample at a time-resolution that is faster than a microorganism division rate. In some time-lapse examples, the time-lapse image corresponds to one or more of the detected in-line hologram and one or more planes of the suspended biological sample. In some examples, the suspended biological sample is obtained from blood, urine, respiratory sample, or saliva. In further examples, the suspended biological sample is a polymicrobial sample. In some examples, the suspended biological sample comprises 10 CFU/ml or less of the at least one microorganism. In further examples, the microorganism comprises one or more bacteria, protozoa, fungi, or combinations thereof.

The foregoing and other objects and features of the disclosure will become more apparent from the following detailed description, which proceeds with reference to the accompanying figures.

DETAILED DESCRIPTION

Figure 1:
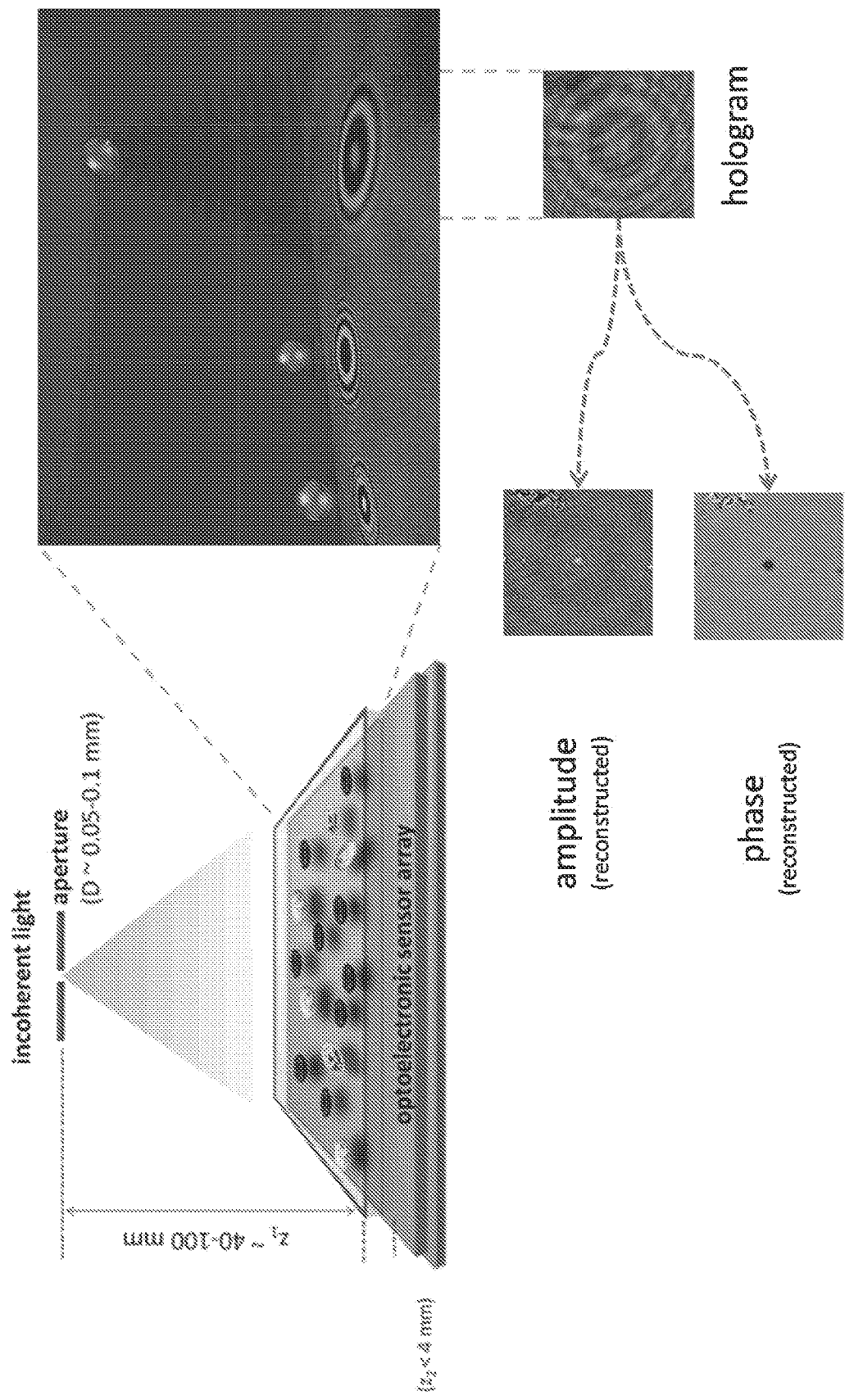
FIG. 1 depicts a lens free imaging using an optoelectronic sensor array to generate a holographic image of sample objects.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a bacterium" includes single or plural bacteria and is considered equivalent to the phrase "comprising at least one bacterium." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. For example, the steps recited in any of the method or process descriptions may be executed in any order and are not necessarily limited to the order presented. Also, any reference to attached, fixed, connected or the like may include permanent, removable, temporary, partial, full and/or any other possible attachment option. Additionally, any reference to without contact (or similar phrases) may also include reduced contact or minimal contact. Furthermore, the connecting lines shown in the various figures contained herein are intended to represent exemplary functional relationships and/or physical couplings between the various elements. It should be noted that alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions.

The disclosed methods, apparatus, and systems should not be construed as limiting. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

In some examples herein, optical beam cross-sectional areas, diameters, or other beam dimensions can be described using boundaries that generally correspond to a zero intensity value, a 1/e value, a $1/e^2$ value, a full-width half-maximum (FWHM) value, or other suitable metric. As used herein, optical illumination refers to electromagnetic radiation at wavelengths of between about 100 nm and 10 µm, and typically between about 200 nm and 2 µm. Optical illumination can be provided at particular wavelengths (typically narrow wavelength bands) or ranges of wavelengths.

As used herein, "AST" is antimicrobial susceptibility testing, antimicrobial agent susceptibility testing, or antibiotic susceptibility testing, and can include MIC (minimum inhibitory concentration) and/or SIR (susceptible, intermediate, resistant).

As used herein, "ID" is identification, such as a process of determining the species identity of a microorganism, such as determining or identifying the genus, species, Gram status, and/or strain of a microorganism. This is distinct from detecting the presence of an unknown microorganism in that it is more specific.

As used herein, "MHA" is Mueller Hinton Agar.

As used herein, "3D" refers to three-dimensional space.

As used herein, "4D" refers to four-dimensional space.

In order to facilitate review of the various embodiments of the disclosure, the following explanations of specific terms are provided:

Administration: To provide or give a subject an agent, such as an antimicrobial agent (such as an antibiotic or antifungal), by any effective route. Exemplary routes of administration include, but are not limited to, oral, injection (such as subcutaneous, intramuscular, intradermal, intraperitoneal, intravenous, intra-articular, and intrathecal), sublingual, rectal, transdermal, intranasal, vaginal and inhalation routes.

Microorganism or microbe: A microscopic organism that in some examples causes disease, for example in a mammal, bird, or fish. Examples of microorganisms include bacteria, fungi (including mold and yeast morphologies), and protozoa.

Sample or specimen: A biological sample or biological specimen, such as those obtained from a subject (such as a human or other mammalian subject, such as a veterinary subjects, for example a subject known or suspected of having an infection). The sample can be collected or obtained using methods well known to those skilled in the art. Samples can contain nucleic acid molecules (such as DNA, cDNA, and RNA), proteins, cell membranes, or combinations thereof. In some examples, the disclosed methods include obtaining the sample from a subject prior to analysis of the sample using the disclosed methods and devices. In some examples, a sample to be analyzed is lysed, extracted, concentrated, diluted, or combinations thereof, prior analysis with the disclosed methods and devices.

Exemplary samples include, without limitation, cells, cell lysates, blood smears, cytocentrifuge preparations, flow-sorted or otherwise selected cell populations, cytology smears, bodily fluids (e.g., blood and fractions thereof such as white blood cells, serum or plasma; saliva; respiratory samples, such as sputum or lavages; urine; cerebrospinal fluid; gastric fluid; sweat; semen; puss; etc.), buccal cells; extracts of tissues, cells or organs, tissue biopsies (e.g., tumor or lymph node biopsies); liquid biopsies; fine-needle aspirates; broscopic lavage; punch biopsies; bone marrow; amniocentesis samples; autopsy material; fresh tissue; vaginal swabs; rectal swabs; and the like. The biological sample may also be a laboratory research sample such as a cell culture sample or supernatant. As used herein, samples can include a sample volume and can be introduced to a container or receptacle that houses or supports the sample volume. Sample volumes can include liquid or particulates of the sample (e.g., microorganisms, if present) obtained from a sampled subject. In typical examples, the liquid and/or particulate portions of the sample can include a mixture with supporting media, such as growth media. The container or receptacle housing the sample can include sample reaction chambers, which can include solid supports (e.g., polycarbonate, silicone, glass, etc.) into which patient sample material is loaded and which can define separations between portions of the sample volume. In typical examples, "sample" can refer to the material of a biological sample, such as when the material is transferred between supporting structures (e.g., introducing a sample to a flow cell). Sample receptacles can also refer to structures that receive and support samples and also structures that receive and support sample containers that house samples.

Subject: Any mammal, such as humans and veterinary subjects, such as, non-human primates, pigs, sheep, cows, dogs, cats, rodents and the like. In one example, a subject is a human subject. In some examples, the subject is known or suspected of having an infection. In some examples, the subject is septic.

Overview

Patient samples, such as blood, respiratory, and other biological samples, are the primary biological starting point for assessing the etiology of a patient's disease and determining the appropriate therapy course for treating that disease. Key to reducing morbidity and mortality is initiating the proper therapeutic treatment of a critically ill patient at the appropriate dosage regimen as soon as possible. The historically weak link in this process is sufficient cultivation of a microbial population in the patient sample to enable identification of pathogen(s) present and to determine which antimicrobial compounds the pathogen(s) will respond to in therapy. Reducing the assay time required to properly identify microorganism(s) in a patient sample and assess their drug sensitivity is crucial to improving patient survival odds.

In many instances, patient samples contain only a single type of microorganism. In other instances, patient samples contain multiple types of microorganisms, such as mixtures of bacteria from differing genera, species, and even strains (also known as "polymicrobial" samples). Diagnostic accuracy is traditionally expressed in terms of sensitivity and specificity. Sensitivity refers to the probability of assigning a diagnostic test as positive when it is in fact, positive (the fraction of true positives), which confound the identification and antimicrobial sensitivity processes. The counter to sensitivity is specificity, which is the rate of obtaining false negative test results. Current methods of identifying unknown microorganisms are prone to failure in both false positive and false negative modes. These difficulties with sensitivity and specificity are typically fostered by factors that impede sample detection, such as noise, crosstalk, borderline resistance, and the like. Traditional analysis methods often trade sensitivity of detection for the specificity of microorganism identification. In other applications, the reverse is true, prioritizing sensitivity over accurate microorganism identification. But to maximize efficiency, and thus improve the odds of achieving a better treatment outcome for the patient, improving sensitivity for detecting the presence of microbial cells as early as possible is desirable. In doing so, clinicians and laboratory personnel can determine which samples may be eliminated from the microbial identification and antimicrobial sensitivity workflow stream due to a true negative reading at the earliest possible time.

Traditional methods for identification (ID) and antimicrobial susceptibility testing (AST) of organisms from clinical specimens typically require overnight subculturing to isolate individual species (e.g., determine if the sample is positive for the presence of pathogenic bacteria, protozoa, and/or fungi) prior to biochemical assay-based identification, followed by growing isolated organisms in the presence of various antimicrobials to determine susceptibilities. Although molecular identification methods can provide organism identification in a few hours directly from clinical specimens as well as resistance marker detection, these methods do not provide the antimicrobial susceptibility information required by clinicians to inform treatment decisions. Studies demonstrating the feasibility of using various sample types including whole blood and respiratory samples have been reported, but sample preparation techniques require further refinement. Current rapid molecular-based diagnostic methods only report identification and genotypic resistance marker results. While available in a couple of hours, these results only provide a partial answer. This leaves the clinician to prescribe overly-broad spectrum empiric therapy while waiting two to four days for conventional antibiotic susceptibility test results before adjusting therapy. The availability of an antimicrobial susceptibility test result in as few as 5 hours or less, as opposed to a few days, potentially decreases morbidity and mortality in critically ill patients due to delays in administration of appropriate therapy. In addition, rapid de-escalation from broad-spectrum empiric therapies to targeted specific antimicrobials could assist antimicrobial stewardship efforts to decrease the emergence and spread of multi-drug resistant organisms (MDROs). By using the disclosed holographic approach to determine which patient samples actually have microorganisms present therein (e.g., as an alternative to overnight culturing), patients who can truly benefit from identification and antimicrobial susceptibility testing can be pinpointed. Only those patients samples deemed positive for the presence of microorganisms would then be subjected to ID and AST evaluation, saving resources and time. Furthermore, in some examples, microorganisms can be precisely quantified, movements tracked, morphological characteristics identified, and/or phenotypic behavior classified.

To address these problems, the disclosed system provides an automated microscopy system designed to provide rapid microorganism detection prior to typical identification and antibiotic susceptibility testing results. An aspect of this system is an optical interrogation platform capable of detecting bacterial and/or fungal growth in a sample obtained directly from a patient without prior overnight culturing. Exemplary samples include blood, respiratory material, urine, CSF, spinal fluid, and other bodily fluids and tissue (such as soft tissue samples and wound material). Samples can contain a very low concentration of microorganisms, so low that direct from patient samples would typically be deemed negative for the presence of microorganisms, despite a patient demonstrating symptoms consistent with an infection. For example a sample may have a target bacterial concentration of as low as about 10 cfu/mL or even 1 cfu/mL. The optical interrogation platform can be integrated into a small (portable) incubator or contain a temperature controlled environmental chamber to ensure normal bacterial growth during the interrogation process.

System

FIG. 1 depicts a lens free imaging system using an optoelectronic sensor array to generate a holographic image of sample objects. Large scale optical inferometry targets objects in a sample reaction chamber (e.g., a flowcell, such as a microfluidic flow cell or perfusion chamber), with incident light. When light waves encounter an object—such as a microbial cell or debris—the light waves are distorted from their original path and the interference or light scatter is recorded by the novel optical system as a hologram. When an interference wave spot changes over a period of time, the system records that perturbation as a growing object. Thus, in a phenotypic assessment of whether a viable microorganism exists in a sample, having multiple sensors to screen a relatively large volume of sample in a short period of time may permit the detection of microorganisms in as little as 1.5 to 2 hours by capturing images 15-30 minutes apart (or faster in some examples) over that period. In principle, microbial cells can be detected within 2-3 doubling times using this process.

An embodiment of the optical interrogation platform includes an in-line holographic setup that includes a single-aperture multi-wavelength illumination and a complementary metal oxide semiconductor (CMOS) sensor having a pixel pitch of 1.12 micrometers. Holograms obtained using the optical interrogation platform are reconstructed-propagated via diffraction theory, then intensity and phase retrieved, for example using the iterative phase retrieval algorithm (such as Gerchberg-Saxton (GS)). A reference wave (illumination) can interact with sample as propagating thru sample and at any point along reference wave, and every point becomes another point source (Huygens), and sensor records interference pattern of all of these waves (e.g., hologram). Because a sensor records only the intensity component of the complex wave function (hologram), phase component needs to be extracted. To gain back phase, it can be reconstructed numerically. Step 1 goes back to complex diffraction pattern in a particular focal plane via diffraction theory—solving Fresnel-Kirchoff integral (using Fresnel approximation or convolutional methods). Step 2 then reconstructs phase via iterative phase retrieval algorithm (such as GS). This platform can be paired with or contain a subsystem which, for certain types of samples (such as whole blood and respiratory samples) performs necessary preparatory steps, including but not limited to dilution, centrifugation, application of an electrical field, and spin-and-resuspension, to reduce amounts of non-bacterial debris load. The optical interrogation platform is scalable in space by "mosaicking" illumination-sensor "pairs" (e.g., multiplexing), thereby providing extensible spatial configurations.

Figure 2A:
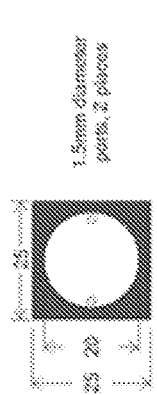
FIG. 2A is a view of a perfusion chamber mounted on a glass microscope slide.
Figure 2A:
Figure 2A:
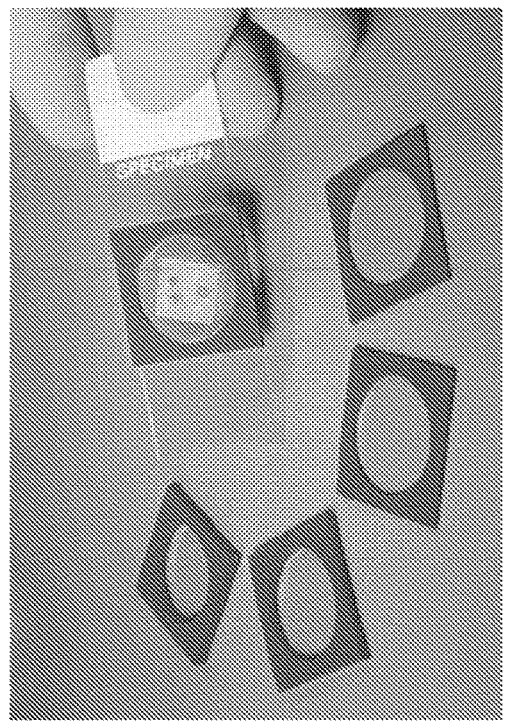
Figure 2B:
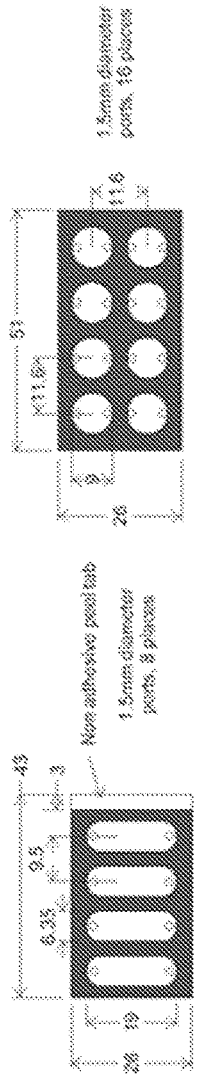
FIG. 2B is a view of alternative perfusion chambers with multiple individual chambers, which can be mounted on a glass microscope slide, for example to analyze multiple samples contemporaneously, a single sample under multiple different media, or combinations thereof.
Figure 2B:
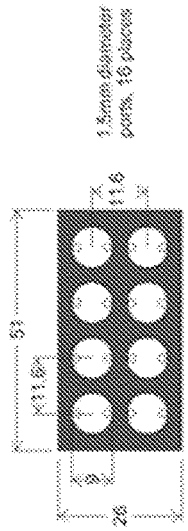

The in-line holographic configuration of a lens-free setup includes multi-wavelength illumination to remove twin-distortion during the phase retrieval stage as well as to improve resolution, but it could be any in-line holographic setup such as multiple illumination apertures, single-wavelength or multi-wavelength illumination, and the like that provides effective resolution of ~1 micro-meter/pixel. Although one embodiment of the optical interrogation platform utilized a perfusion chamber mounted on top of a standard glass microscopy slide, the platform may be designed to support imaging of other sample reaction chambers (e.g., flowcells, such as microfluidic channels or perfusion chambers) of a different configuration. FIG. 2A is a view of exemplary sample reaction chamber (e.g., perfusion chamber) mounted on glass microscope slides. FIG. 2B shows other exemplary perfusion chambers that can be used.

Figure 3:
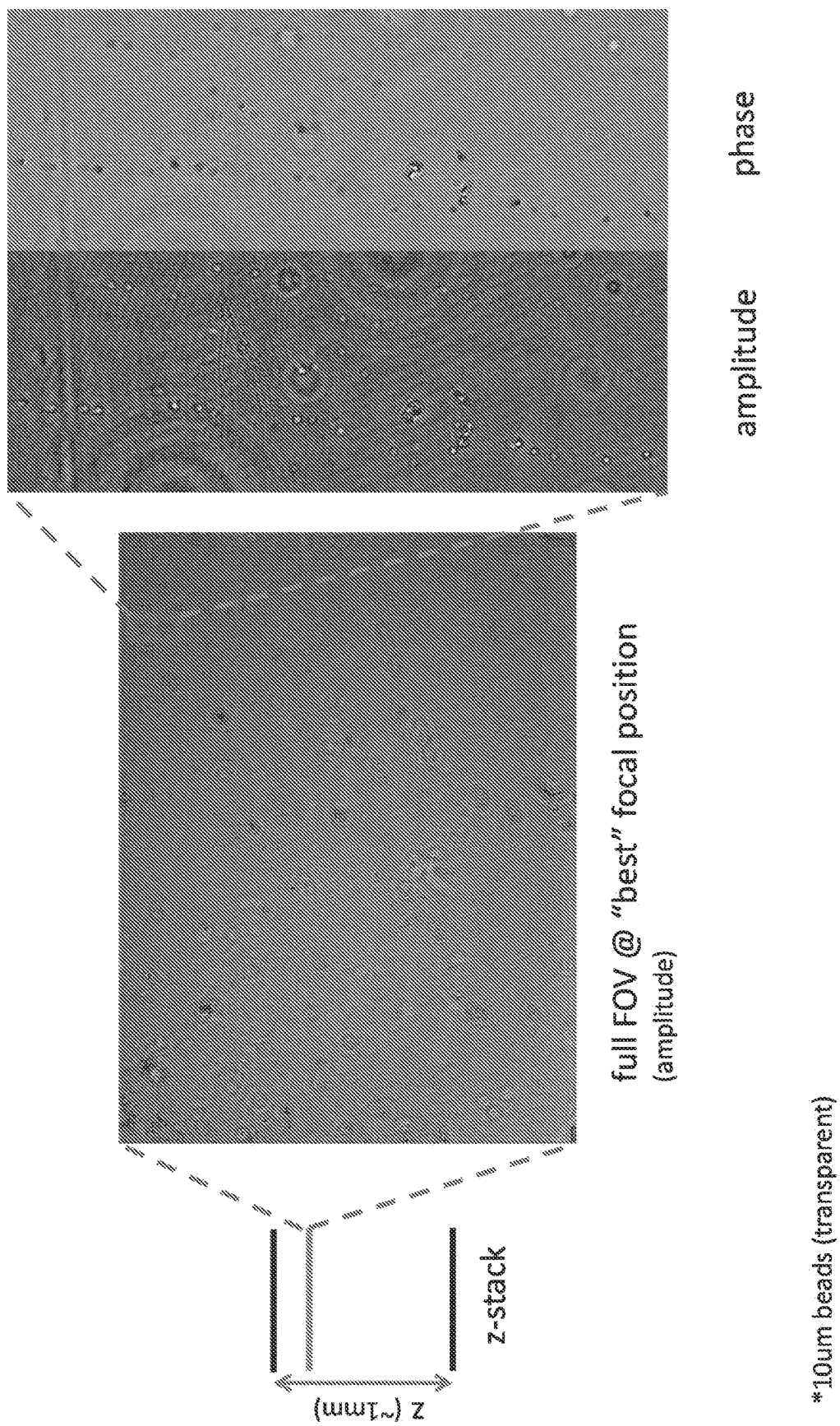
FIG. 3 shows images obtained showing proof of concept of the optical interrogation platform using transparent silicone beads.

As previously noted, the optical interrogation platform automates growth detection of microorganisms present in very low concentrations. In general, given the system's acquisition setup, each object suspended in a 3-dimensional (3D) volume has an optimal focal plane (plane of highest variance) at any given time. The optimal focal plane can be found automatically for each object in the imaged volume for every time of the time-lapse sequence. Then, tracking or equivalent spatial differencing techniques can be employed to detect changes. Various optical transforms are possible to return to object. Because optical transforms underlying hologram construction are linear operators, multiple holograms can be obtained and manipulate without loss of information, for example to determine the presence or identification of a microbe, or measure growth of a microbe over time. FIG. 3 shows images obtained showing proof of concept of the optical interrogation platform using beads. The beads mimicking bacteria, protozoa, or fungi in a patient sample can be "seen" using holograms, but are not visible by standard bright field microscopy. One hologram can be stored per 3D stack. The holographic image of the volume may be stored, and then later the focal plane can be reconstructed numerically. The holograms may be stored as TIFF, JPEG, or other files routinely used in imaging.

In a "mosaicked" embodiment, the optical interrogation platform can be extended to conduct simple antimicrobial susceptibility testing. This is accomplished by dedicating at least one microfluidic channel to serving as a growth control channel containing a sample in the absence of antimicrobial agent. One or more other microfluidic channels containing samples with antimicrobial agents added at an appropriate concentrations may be utilized to assess antimicrobial susceptibility. For example, antibiotic susceptibility may be assessed by pre-mixing antibiotics with sample before introducing the mixture to one or more sample reaction chambers (e.g., flowcell, such as a microfluidic flowcell or perfusion chamber). Alternatively, antibiotics may be added after a sample has been deposited into the sample reaction chamber, or antibiotics may diffuse into contact with the sample from a dried-down state in the sample reaction chamber. During growth supporting conditions, microbial replication in the "growth control" channel is compared to replication in one or more antimicrobial channels over time can yield first-order susceptibility/resistance information.

Another embodiment of the optical interrogation platform supports a multi-channel scanning configuration (a tiled or "mosaicked" arrangement) can be extended with "growth control" channels that use selective media. Growth information from these channels, in conjunction with a standard "growth control" channel, can be used to infer bacterial families and even species. In another embodiment, the optical interrogation platform permits microbial differentiation based on organism morphology. Under certain optical resolution (~0.5 um/pixel), the platform can be used to conduct morphological analysis to differentiate morphology of individual bacterial cells within each micro-colony. Such information can be reported to a clinician.

In some embodiments, microorganism detection is achieved by simultaneously scanning a sample volume as large as ~300 microliters (μL) in a single optical field-of-view of up to 30 mm$^2$ of surface area and up to 1 mm depth. The system can perform time-lapse imaging of the same volume without mechanical motion at acquisition rates that are much higher than microbial division rates. Thus, the system enables the imaging of bacteria faster than a small number of their doubling events, such as fewer than 4 doubling events, fewer than 3 doubling events, or fewer than two doubling events. Some bacteria have a doubling time of about 15-30 minutes, meaning that detection of the presence of such bacteria in a patient's sample could be achieved by the system in about 30 to 45 minutes.

The detection of a microorganism in a sample in such a short period of time permits clinicians to rapidly determine which patient samples should be further subjected to multiplexed automated single cell digital microscopy. One such digital microscopy system is the fully automated, microscopy-based system disclosed in U.S. patent publication no. US 2017/0023599 (herein incorporated by reference), which can perform bacterial or yeast identification in about one (1) hour and AST in about five (5) or fewer hours.

Methods of Identifying Microorganisms

The disclosed systems and devices can be used in methods to aid in the diagnosis of bacteremia and fungemia. They can also be used for susceptibility testing of specific pathogenic bacteria commonly associated with or causing bacteremia. Results can be used in conjunction with other clinical and laboratory findings.

The disclosed methods can be used to quickly determine if the patient has a microbial infection, and in some examples also identify the microbes infecting the patient, and identify which antimicrobial agents are likely to be effective in treating the infection. Such methods are faster than currently available assays. In currently available assays, a patient sample is incubated overnight in the presence of a culture medium (such as at least 8 hours, at least 10 hours, at least 12 hours, or at least 18 hours, such as 8 to 24 hours or 8 to 12 hours), to allow for microbes present in the sample to grow and multiply. If this results in a positive result (i.e., microbes are present), then additional assays are used to identify the microbe, identify an effective antimicrobial agent to administer to the patient to treat their infection, and determine a minimal inhibitory concentration (MIC) of antimicrobial agent to use. In contrast, in representative examples, the disclosed methods and systems do not require overnight incubation of the patient sample (e.g., in a culture medium) to determine whether the patient sample is positive (i.e., microbes are present). In some embodiments, the disclosed methods identify the microbe(s) in the patient sample (e.g., the genus, species, Gram status and/or strain of the microbe(s)), and identify an effective antimicrobial agent to administer to the patient to treat their infection. In some examples, the disclosed methods take less than 3 hours to complete, such as less than 2 hours, less than 1.5 hours or about 1.5 hours, such as 1 to 3 hours, or 1.5 to 2 hours. For example, using the disclosed methods, it can take less than 3 hours, or less than 2 hours, such as 1.5 to 3 hours, or 1.5 to 2 hours to determine if the sample is positive for bacteria, protozoa and/or fungi. For example, using the disclosed methods, it can take less than 3 hours, such as less than 2 hours, such as 2 to 3 hours, or 1.5 to 2 hours to identify the bacteria, protozoa, and/or fungi in the sample. For example, using the disclosed methods, it can take less than 6 hours, less than 5 hours, or less than 4 hours, such as 3 to 6 hours, or 4 to 5 hours to identify the antimicrobial that the bacteria, protozoa, and/or fungi in the sample are sensitive to (e.g., will kill the bacteria, protozoa, and/or fungi).

Patients can include human and veterinary subjects, such as cats, dogs, cows, pigs, horses, sheep, goats, chickens, turkeys, and other birds, fish, and the like. In some examples, a patient is one who is known to have or is suspected of having an infection (such as a bacterial or fungal infection). In one example, the patient is septic. Patient samples include but are not limited to blood (e.g., whole blood, plasma, or serum), respiratory samples (such as bronchoalveolar lavage, oropharyngeal swab, nasopharyngeal swab, or sputum), saliva, urine, rectal swab, vaginal swab, tissue samples, or other biological specimens (such as those described herein).

In some examples, the patient sample contains only a single type of microorganism. In other instances, the patient sample contains multiple types of microorganisms, such as mixtures of bacteria, protozoa, and/or fungi from differing genera, species, and even strains (also known as "polymicrobial" samples), such as at least 2, at least 3, at least 4 or at least 5 different types of bacteria, protozoa, and/or fungi. In some examples, the patient sample contains bacteria that are about 0.2 to 5 microns in width or diameter, such as 0.5 to 5 microns in width or diameter, 1 to 2 microns in width or diameter, or 0.5 to 1 microns in width or diameter. In some examples, a patient sample has a bacterial, protozoal, and/or fungal concentration of less than 100 CFU/mL, less than 50 CFU/mL, or less than 10 CFU/mL, such as 1 to 20 cfu/ML, 1 to 100 CFU/mL, or 10 to 200 CFU/mL, such as about 5 CFU/mL, 10 CFU/mL, about 20 CFU/mL, about 30 CFU/mL, about 40 CFU/mL, about 50 CFU/mL, about 60 CFU/mL, about 70 CFU/mL, about 80 CFU/mL, about CFU/mL, or about 100 CFU/mL. Thus, in some examples, the method is capable of detecting bacteria, protozoa, and/or fungi at less than 100 CFU/mL, less than 50 CFU/mL, or less than 10 CFU/mL, such as 1 to 20 cfu/ML, 1 to 100 CFU/mL, or 10 to 200 CFU/mL, such as about 5 CFU/mL, 10 CFU/mL, about 20 CFU/mL, about 30 CFU/mL, about 40 CFU/mL, about 50 CFU/mL, about 60 CFU/mL, about 70 CFU/mL, about 80 CFU/mL, about CFU/mL, or about 100 CFU/mL.

In some examples, the patient sample is used directly. In other examples, the patient sample is subjected to one or more pre-processing steps prior to imaging the sample. For example, the patient sample can be concentrated, diluted, filtered, centrifuged, and/or separated before analysis. In one example, the patient sample is lysed prior to analysis, for example to remove or reduce the number of non-bacterial or non-fungal cells in the sample (e.g., to lyse blood cells). In some examples, the patient sample is concentrated prior to analysis, for example by centrifugation, which can also remove debris from the sample. In one example, the patient sample is subjected gel electrofiltration (GEF) (for example, to remove or reduce lysed cells and debris in the sample). GEF is a process of sample preparation that relies on application of an electrical field to cause sample debris present in a sample to be separated from microorganism cells. Likewise, membrane assisted purification may be used in some embodiments, such that in response to an electrical potential, sample contaminants enter a porous filter medium through one or more walls of a well disposed in the filter medium, thereby separating them from cells of interest in the sample.

The patient sample (or portion thereof) is loaded in or introduced into one or more solid supports (e.g., sample reaction chamber, such as a flowcell, microfluidic chancel, or perfusion chamber) of a sample container that allows microbes to be visualized using the disclosed holographic methods. In one example, the support includes one or more flowcells, microfluidic channels, perfusion chambers, or combinations thereof, such as one on a microscope slide (or other solid support that is optically transparent (e.g., glass or plastic) and, non-toxic to microorganisms). In some example, the perfusion chamber is a CoverWell™ perfusion chamber (see FIGS. 2A and 2B). An exemplary perfusion chamber mounted on a microscope slide is shown in FIG. 2A. The perfusion chamber has a 20 mm diameter, with two ports (which allow for introduction of the sample, for example in a MHA gel suspension, as well as removal of materials). In this example, the volume of the perfusion channel is about 300 uL, with an effective imaging area of about 16 mm$^2$ at 0.9 um/pixel. One skilled in the art will appreciate that other perfusion chambers can be used, such as other shapes (e.g., square, rectangular, oval, etc.). In addition, a single slide can include multiple individual sample reaction chambers, for example to allow multiple samples to be analyzed contemporaneously, to allow a single sample to be analyzed in the presence of different reagents (e.g., different growth media and/or antimicrobial agents), or combinations thereof (FIG. 2B).

After introducing the sample into a micro-fluidic channel, a perfusion chamber, or both (for example using a manual or automated pipettor), the cells in the sample can be immobilized, for example by entombing them in three-dimensional space in a growth medium containing a gelling or solidification agent, such as agar or agarose. In some embodiments, the entombing creates a microenvironment around the immobilized microorganism, the characteristics of which are not influenced by neighboring microorganisms during the identification and/or susceptibility testing periods. In some examples, the method includes retaining the microorganism on a detection surface of the support, thereby producing a retained microorganism, and subsequently introducing a gel medium (such as one containing agar) into the micro-fluidic channel, perfusion chamber, or both, wherein the gel medium is in contact with the retained microorganism following introduction into the micro-fluidic channel, perfusion chamber, or both; immobilizing the retained microorganism in the micro-fluidic channel, perfusion chamber, or both at the same location where the microorganism is retained, to produce an immobilized microorganism, wherein offspring of the immobilized microorganism remain over time at a location with the immobilized microorganism; and incubating the immobilized microorganism for a period of time to allow for growth of the microorganism.

The sample and microorganisms therein can be incubated and immobilized in the growth media in the sample reaction chamber at various temperatures, which in some examples is selected based on the microorganism thought to be present in the sample. In some examples, the immobilized microorganism are incubated at a temperature of at least 15° C., at least 20° C., at least 25° C., at least 30° C., or at least 37° C., such as 20° C. to 40° C., or 25° C. to 37° C.

The gel medium in which the microorganisms (and their offspring) are immobilized in some examples does not include antimicrobial agents. In one example, the gel medium in which the microorganisms (and their offspring) are immobilized is MHA, trypticase soy agar, or any other non-selective culturing media, which permits growth of most microorganisms. This can be referred to as the "growth control" channel or chamber. Thus, if microorganisms are present in the sample, they should grow and be detectable in this medium.

In some examples, the cells of the sample are not immobilized and microorganisms can be identified and tracked.

For some samples, clinical decisions may be require an estimate of the concentration of a pathogen (or multiple pathogens) in the sample, which is usually reported on log-scale. For example, a clinician may determine that a urine sample is negative if the concentration of a particular pathogen is less than $10^4$ cfu/mL. Therefore, treatment decisions may be made based on such information. In some examples herein, reporting of such information is allowed via direct optically resolved observation of the sample with accuracy that is better than half-log for each target species in the sample (including polymicrobial samples). For example, urines are not typically pathogenic if less than $10^4$. Similarly, respiratory samples are not typically pathogenic if less than $10^3$. But, normal methods of quantifying such samples is very poor, with samples plated and colonies counted, leading to highly error prone results, such as merely obtaining second derivative of what was actually in the sample. In examples herein, time-evolved holographic results can be used to directly discern particles from bacteria, which can produce cost-effective and accurate quantity estimates.

In some examples, a sample is introduced into multiple sample reaction chambers (e.g., flowcell or perfusion chamber) of a sample container, such that at least one sample reaction chamber does not include antimicrobial agents, and the others can include different antimicrobial agents, for example to assess antimicrobial susceptibility. In some examples, the antimicrobial agents selected are based on the identification of the microorganism(s) present in the sample. For example, antibiotic susceptibility may be assessed by pre-mixing antimicrobial agents with the patient sample before introducing the mixture to one or more sample reaction chambers. Alternatively, antimicrobial agents may be added after a patient sample has been introduced into the sample reaction chambers, or antibiotics and/or antifungal agents may diffuse into contact with the patient sample in the sample reaction chambers. During growth supporting conditions, microbial replication in the "growth control" channel is compared to replication in one or more "antimicrobial channels" over time can yield first-order susceptibility/resistance information. In some examples, different amounts of the same antimicrobial agent are used (e.g., serial dilution). In some example, the media containing the sample includes one or more of the following antimicrobial agents: amikacin, ampicillin, ampicillin-sulbactam, aztreonam, ceftazidime, ceftaroline, cefazolin, cefepime, ceftriaxone, ciprofloxacin, colistin, daptomycin, oxycycline, erythromycin, ertapenem, gentamicin, imipenem, linezolid, meropenem, minocycline, piperacillin-tazobactam, trimethoprim-sulfamethoxazole, tobramycin, vancomycin, or combinations of two or more thereof. Other antimicrobial agents that can be used also include aminoglycosides (including but not limited to kanamycin, neomycin, netilmicin, paromomycin, streptomycin, and spectinomycin), ansamycins (including but not limited to rifaximin), carbapenems (including but not limited to doripenem), cephalosporins (including but not limited to cefadroxil, cefalotin, cephalexin, cefaclor, cefprozil, fecluroxime, cefixime, cefdinir, cefditoren, cefotaxime, cefpodoxime, ceftibuten, and ceftobiprole), glycopeptides (including but not limited to teicoplanin, telavancin, dalbavancin, and oritavancin), lincosamides (including but not limited to clindamycin and lincomycin), macrolides (including but not limited to azithromycin, clarithromycin, dirithromycin, roxithromycin, telithromycin, and spiramycin), nitrofurans (including but not limited to furazolidone and nitrofurantoin), oxazolidinones (including but not limited to posizolid, radezolid, and torezolid), penicillins (including but not limited to amoxicillin, flucloxacillin, penicillin, amoxicillin/clavulanate, and ticarcillin/clavulanate), polypeptides (including but not limited to bacitracin and polymyxin B), quinolones (including but not limited to enoxacin, gatifloxacin, gemifloxacin, levofloxacin, lomefloxacin, moxifloxacin, naldixic acid, norfloxacin, trovafloxacin, grepafloxacin, sparfloxacin, and temafloxacin), suflonamides (including but not limited to mafenide, sulfacetamide, sulfadiazine, sulfadimethoxine, sulfamethizole, sulfamethoxazole, sulfasalazine, and sulfisoxazole), tetracyclines (including but not limited to demeclocycline, doxycycline, oxytetracycline, and tetracycline), and others (including but not limited to clofazimine, ethambutol, isoniazid, rifampicin, arsphenamine, chloramphenicol, fosfomycin, metronidazole, tigecycline, and trimethoprim), or any combination of two or more thereof. Further antimicrobial agents include amphotericin B, ketoconazole, fluconazole, itraconazole, posaconazole, voriconazole, anidulafungin, caspofungin, micafungin, flucytosine, or any combination of two or more thereof.

In some examples, a sample is introduced into multiple sample reaction chambers of a sample container, such that at least one sample reaction chamber does not include antimicrobial agents, and the others can include different selective and differential growth media, for example to identify the microorganisms present in the sample. Some growth media only supports growth and replication of particular microorganisms or types of microorganisms. Examples of selective and differential media include blood agar, Eosin Methylene Blue (EMB) agar, mannitol salt agar, MacConkey agar, phenylethyl alcohol (PEA) agar, and YM agar. For example, EMB agar inhibits Gram-positive organisms, and is thus selective for Gram-negative species. MacConkey agar is also selective for Gram-negative species and differential with respect to lactose fermentation. Mannitol salt agar (7.5% NaCl) is selective for staphylococci and differential with respect to mannitol fermentation, wherein fermentation of mannitol is only seen in the pathogenic species of *Staphylococcus*. PEA agar is a selective medium which inhibits the growth of most Gram negative organisms. For example, MacConkey agar can be used to select for Gram-negative bacteria (e.g., permits growth of Gram-negative bacteria), mannitol salt agar can be used to select for Gram-positive bacteria (such as *Staphylococcus*), and YM agar can be used to select for yeast. Thus, detection of growth in a particular media, and in some examples not in other media, can allow for the identification of the microorganism. For example, the identification of a microorganism, for example determining its genus, species, Gram status and/or strain can be assessed by pre-mixing a particular growth media with the patient sample before introducing the mixture to one or more sample reaction chambers. Alternatively, particular growth media may be added after a patient sample has been introduced into the sample reaction chamber, or selective agents may diffuse into contact with the patient sample in the sample reaction chamber. During growth supporting conditions, microbial replication in the "growth control" channel is compared to replication in one or more "selective media" channels over time can yield microorganism identification information. In some examples, alternatively or in addition to the use of "selective media" channels, the microorganisms are identified by morphology (e.g., shape, size) information obtained using the disclosed methods.

In some examples, the method includes determining the number of minimum number of microbes needed in the "growth control" channel to ensure that all of the channels containing the patient sample will have detectable microbes, if present in the sample. For example, serial dilutions can be performed.

After the microorganisms are immobilized, they (and their offspring) are imaged using the disclosed holographic imaging methods. Images of one or more (such as 1-100, for example, 2-25, 10-40, 30-80, or 50-100) fields of view (scaled depending on the volume of the channel to be interrogated) of one or more microorganisms are captured. Multiple images of the same field of view may be captured, for example under one or more different imaging modalities. For example, images can be obtained over a period of seconds, to minutes, to hours, such as every 5 minutes, 10 minutes, 15 minutes, 20 minutes, 30 minutes, or 60 minutes. In some examples, images (such as images of the "growth control" channel) are obtained for at least 1 hour, at least 1.5 hours, at least 2 hours, at least 3 hours, at least 4 hours, at least 5 hours, at least 6 hours, at least 7 hours, at least 8 hours, at least 9 hours, or at least 10 hours, such as 1 to 4 hours, 1 to 2 hours, 1.5 to 2 hours, or 2 to 4 hours. The results from the "growth control" channel allow for the determination as to whether the patient sample contains bacteria, protozoa, and/or fungi, that is, whether the sample is "positive".

In some examples, during a microbial identification assay period, images are obtained about every 5-30 minutes (such as about every 5 minutes, 10 minutes, 15 minutes, 20 minutes, 25 minutes, or 30 minutes) for about 1 to 8 hours, such as up to about 1.5 hours, 2 hours, 3 hours, 4 hours, 4.5 hours, 5 hours, 6 hours, 7 hours, or 8 hours. In some examples during this stage, the images are subjected to morphological or other analysis (such as morphokinetic analysis) to identify characteristics of the imaged microorganisms, including one or more of noise, cross-talk, and microorganism morphology. The results from the "selective media" channel allow for the identification of the microorganisms (e.g., Gram status, genus, species, and/or strain) present in the patient sample.

In some examples, during an AST assay period, images are obtained about every 5-30 minutes (such as about every 5 minutes, 10 minutes, 15 minutes, 20 minutes, 25 minutes, or 30 minutes) for about 1 to 6 hours, such as about 1.5 hours, 2 hours, 3 hours, 4 hours, 4.5 hours, 5 hours, or 6 hours, creating a time-lapse record of microorganism growth. During the AST process, various microorganism clone features can be measured, such as morphology and division rates and used for analysis. In some examples, the growth of the microorganisms is measured qualitatively or quantitatively, for example by measuring the growth (or amount of growth), lack of growth, or lysis of the microorganisms. Based on the behavior of the microorganisms over time in the presence of the one or more antimicrobials (for example, compared to a control that is not exposed to the antimicrobial(s)), a determination of susceptibility (or indeterminate susceptibility) or resistance of the identified microorganisms to each antimicrobial is made. The results from the "antimicrobial channel" allow for the determination as to which antibiotic(s) the microorganism in the sample is susceptible to. Thus, in some embodiments, the system reports susceptibility, intermediate, or resistance to one or more antimicrobials. In some embodiments, the following resistance phenotypes are reported by the system in response to AST data analysis: Methicillin-resistant *Staphylococcus aureus* (MRSA), methicillin-resistant staphylococci (MRS), vancomycin-resistant *S. aureus* (VRSA), vancomycin-resistant *Enterococcus* species (VRE), high-level aminoglycoside resistance (HLAR) and macrolide-lincosamide-streptogramin B resistance (MLSb). Upon this determination, the subject from whom the sample was obtained can be administered a therapeutically effective amount of the identified antibiotic(s).

Exemplary Microbes Detected

The disclosed methods and systems can be used to detect various Gram-positive and Gram-negative bacteria, protozoa, and fungi (e.g., yeasts), including but not limited to: *Staphylococcus aureus, Staphylococcus lugdunensis*, coagulase-negative *Staphylococcus* species (*Staphylococcus epidermidis, Staphylococcus haemolyticus, Staphylococcus hominis, Staphylococcus capitis*, not differentiated), *Enterococcus faecalis, Enterococcus faecium* (*Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (*Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella* spp. (*Klebsiella pneumoniae, Klebsiella oxytoca*, not differentiated), *Escherichia coli, Enterobacter* spp. (*Enterobacter cloacae, Enterobacter aerogenes*, not differentiated), *Proteus* spp. (*Proteus mirabilis, Proteus vulgaris*, not differentiated), *Citrobacter* spp. (*Citrobacter freundii, Citrobacter koseri*, not differentiated), *Serratia marcescens, Candida albicans*, and *Candida glabrata*.

Other specific bacteria that can be detected with the disclosed systems and methods, include without limitation: *Acinetobacter baumannii, Actinobacillus* spp., Actinomycetes, *Actinomyces* spp. (such as *Actinomyces israelii* and *Actinomyces naeslundii*), *Aeromonas* spp. (such as *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (such as *Bacillus anthracis, Bacillus cereus, Bacillus subtilis, Bacillus thuringiensis*, and *Bacillus stearothermophilus*), *Bacteroides* spp. (such as *Bacteroides Bartonella* spp. (such as *Bartonella bacilliformis* and *Bartonella henselae*, *Bifidobacterium* spp., *Bordetella* spp. (such as *Bordetella pertussis, Bordetella parapertussis*, and *Bordetella bronchiseptica*), *Borrelia* spp. (such as *Borrelia recurrentis*, and *Borrelia burgdorferi*), *Brucella* sp. (such as *Brucella abortus, Brucella canis, Brucella melintensis* and *Brucella suis*), *Burkholderia* spp. (such as *Burkholderia pseudomallei* and *Burkholderia cepacia*), *Campylobacter* spp. (such as *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp. *Coxiella burnetii, Corynebacterium* spp. (such as, *Corynebacterium diphtheriae, Corynebacterium jeikeum* and *Corynebacterium*), *Clostridium* spp. (such as *Clostridium perfringens, Clostridium difficile, Clostridium botulinum* and *Clostridium tetani*), *Eikenella corrodens, Enterobacter* spp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* spp. (such as *Enterococcus faecalis* and *Enterococcus faecium*) *Ehrlichia* spp. (such as *Ehrlichia chafeensia* and *Ehrlichia canis*), *Erysipelothrix rhusiopathiae, Eubacterium* spp., *Francisella tularensis, Fusobacterium nucleatum, Gardnerella vaginalis, Gemella morbillorum, Haemophilus* spp. (such as *Haemophilus influenzae, Haemophilus ducreyi, Haemophilus aegyptius, Haemophilus parainfluenzae, Haemophilus haemolyticus* and *Haemophilus parahaemolyticus*, *Helicobacter* spp. (such as *Helicobacter pylori, Helicobacter cinaedi* and *Helicobacter fennelliae*), Kingella *kingii, Klebsiella* spp. (such as *Klebsiella pneumoniae, Klebsiella granulomatis* and *Klebsiella oxytoca*), *Lactobacillus* spp., *Listeria monocytogenes, Leptospira interrogans, Legionella*

*pneumophila, Leptospira interrogans, Peptostreptococcus* spp., *Moraxella catarrhalis, Morganella* spp., *Mobiluncus* spp., *Micrococcus* spp., *Mycobacterium* spp. (such as *Mycobacterium leprae, Mycobacterium tuberculosis, Mycobacterium intracellulare, Mycobacterium avium, Mycobacterium bovis,* and *Mycobacterium marinum*), *Mycoplasm* spp. (such as *Mycoplasma pneumoniae, Mycoplasma hominis,* and *Mycoplasma genitalium*), *Nocardia* spp. (such as *Nocardia asteroides, Nocardia cyriacigeorgica* and *Nocardia brasiliensis*), *Neisseria* spp. (such as *Neisseria gonorrhoeae* and *Neisseria meningitidis*), *Pasteurella multocida, Plesiomonas shigelloides. Prevotella* spp., *Porphyromonas* spp., *Prevotella melaninogenica, Proteus* spp. (such as *Proteus vulgaris* and *Proteus mirabilis*), *Providencia* spp. (such as *Providencia alcalifaciens, Providencia rettgeri* and *Providencia stuartii*), *Pseudomonas aeruginosa, Propionibacterium acnes, Rhodococcus equi, Rickettsia* spp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* spp., *Serratia marcescens, Stenotrophomonas maltophilia, Salmonella* spp. (such as *Salmonella enterica, Salmonella typhi, Salmonella paratyphi, Salmonella enteritidis, Salmonella cholerasuis* and *Salmonella typhimurium*), *Serratia* spp. (such as *Serratia marcesans* and *Serratia liquifaciens*), *Shigella* spp. (such as *Shigella dysenteriae, Shigella flexneri, Shigella boydii* and *Shigella sonnei*), *Staphylococcus* spp. (such as *Staphylococcus aureus, Staphylococcus epidermidis, Staphylococcus hemolyticus, Staphylococcus saprophyticus*), *Streptococcus* spp. (such as *Streptococcus pneumoniae* (for example chloramphenicol-resistant serotype 4 *Streptococcus pneumoniae,* spectinomycin-resistant serotype 6B *Streptococcus pneumoniae,* streptomycin-resistant serotype 9V *Streptococcus pneumoniae,* erythromycin-resistant serotype 14 *Streptococcus pneumoniae,* optochin-resistant serotype 14 *Streptococcus pneumoniae,* rifampicin-resistant serotype 18C *Streptococcus pneumoniae,* tetracycline-resistant serotype 19F *Streptococcus pneumoniae,* penicillin-resistant serotype 19F *Streptococcus pneumoniae,* and trimethoprim-resistant serotype 23F *Streptococcus pneumoniae,* chloramphenicol-resistant serotype 4 *Streptococcus pneumoniae,* spectinomycin-resistant serotype 6B *Streptococcus pneumoniae,* streptomycin-resistant serotype 9V *Streptococcus pneumoniae,* optochin-resistant serotype 14 *Streptococcus pneumoniae,* rifampicin-resistant serotype 18C *Streptococcus pneumoniae,* penicillin-resistant serotype 19F *Streptococcus pneumoniae,* or trimethoprim-resistant serotype 23F *Streptococcus pneumoniae*), *Streptococcus agalactiae, Streptococcus mutans, Streptococcus pyogenes,* Group A streptococci, *Streptococcus pyogenes,* Group B streptococci, *Streptococcus agalactiae,* Group C streptococci, *Streptococcus anginosus, Streptococcus equismilis,* Group D streptococci, *Streptococcus bovis,* Group F streptococci, and *Streptococcus anginosus* Group G streptococci), *Spirillum* minus, *Streptobacillus moniliformi, Treponema* spp. (such as *Treponema carateum, Treponema petenue, Treponema pallidum* and *Treponema endemicum, Tropheryma whippelii, Ureaplasma urealyticum, Veillonella* sp., *Vibrio* spp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* spp. (such as *Yersinia enterocolitica, Yersinia pestis,* and *Yersinia pseudotuberculosis*) and *Xanthomonas maltophilia* among others.

Exemplary fungi that can be detected with the disclosed systems and methods, include without limitation: *Candida* spp. (such as *Candida albicans, Candida glabrata, Candida tropicalis, Candida parapsilosis,* and *Candida krusei*), *Aspergillus* spp. (such as *Aspergillus fumigatous, Aspergillus flavus, Aspergillus clavatus*), *Cryptococcous* spp. (such as *Cryptococcus neoformans, Cryptococcus gattii, Cryptococcus laurentii,* and *Cryptococcus albidus*), *Fusarium* spp. (such as *Fusarium oxysporum, Fusarium solani, Fusarium verticillioides,* and *Fusarium proliferatum*), *Rhizopus oryzae, Penicillium marneffei, Coccidiodes immitis,* and *Blastomyces dermatitidis*.

Exemplary protozoa include, that can be detected with the disclosed systems and methods, include without limitation: *Plasmodium* (e.g., *Plasmodium falciparum*), *Leishmania, Acanthamoeba, Giardia, Entamoeba, Cryptosporidium, Isospora, Balantidium, Trichomonas, Trypanosoma* (e.g., *Trypanosoma brucei*), *Naegleria,* and *Toxoplasma*.

Example

A micro-fluidic channel was constructed by placing a cover well on top of a glass microscopy slide measuring about 20 mm in diameter and 1 mm in height. A patient sample was simulated by diluting an *E. coli* 25922 isolate into Mueller-Hinton agar suspension. The concentration of bacterial isolate was chosen such that there were approximately $10^2$ bacteria per mL. The bacterial-agar suspension was premixed and pipetted into an inlet opening on top of the cover well. Thereafter, the bacterial-agar suspension was subjected to a phase change to solidify the agar and suspend the bacteria in three-dimensional space. Prior to the beginning of image acquisition, the micro-fluidic channel was placed inside an incubator for 1 hr to promote the growth phase of the suspended bacteria.

Figure 4:
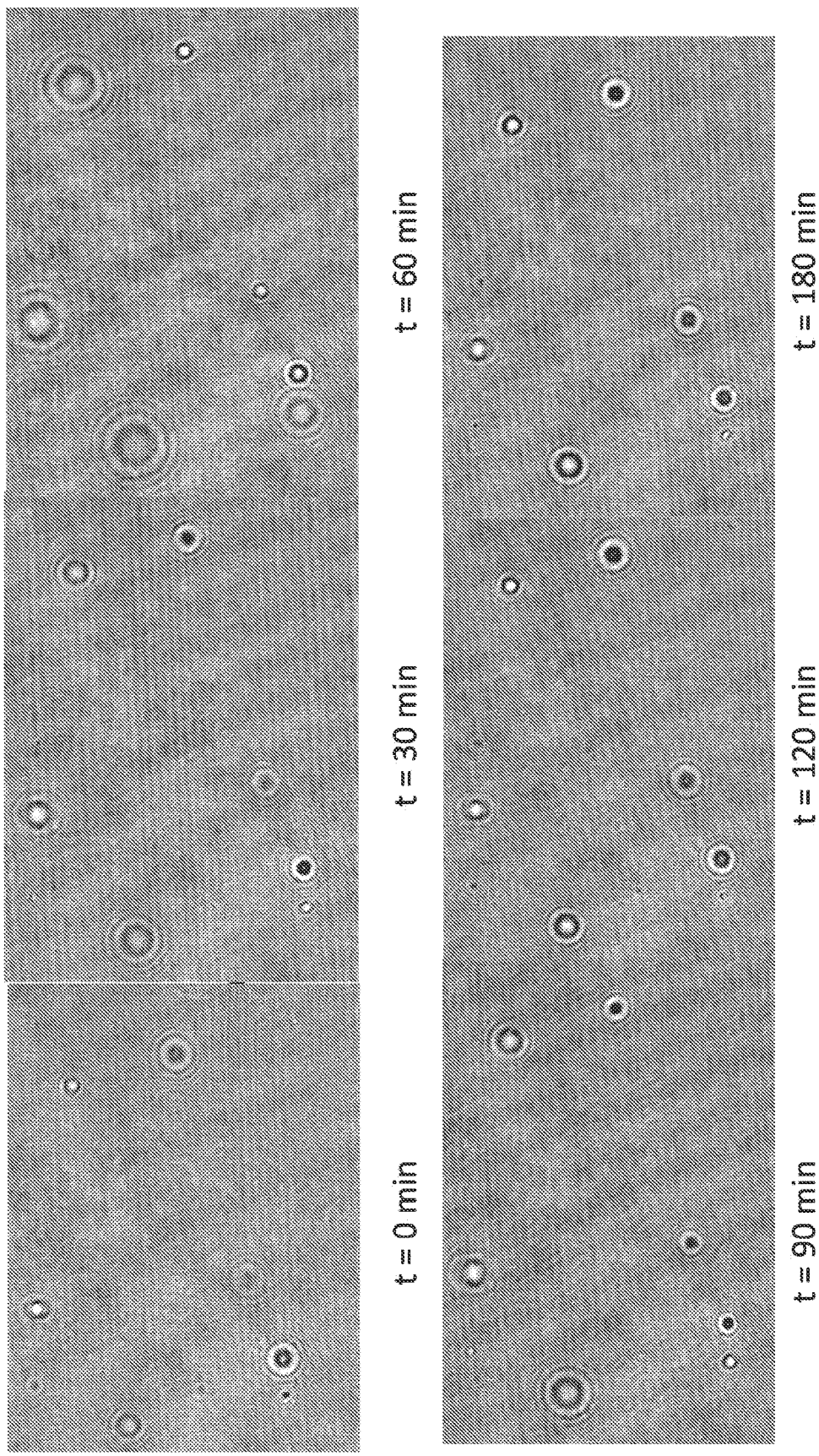
FIG. 4 shows images obtained by the optical interrogation platform imaging *E. coli* growth over a period of 0 to 180 minutes.
Figure 5:
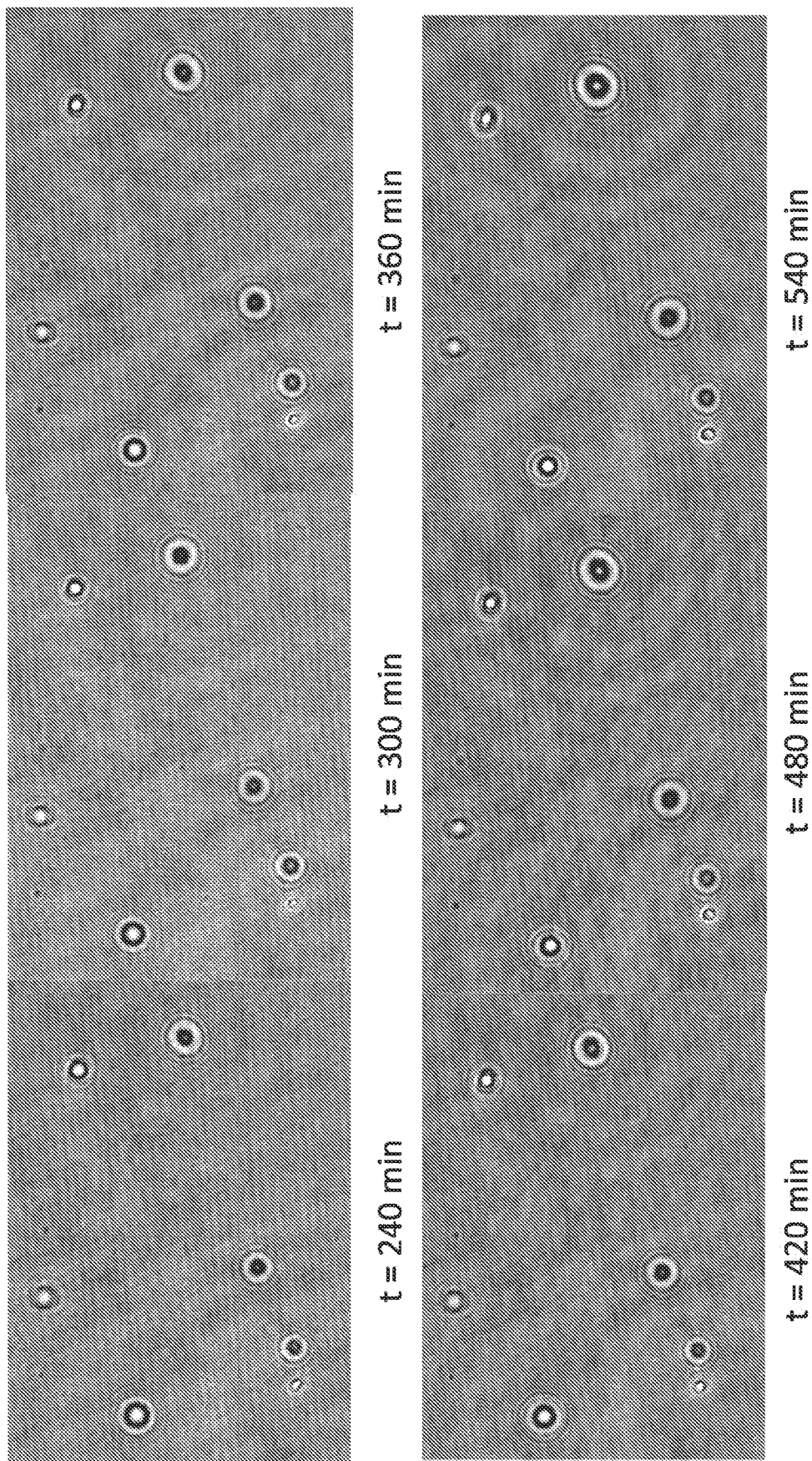
FIG. 5 shows images obtained by the optical interrogation platform imaging *E. coli* growth during a period from 240 to 540 minutes.

Time-lapse imaging was conducted on a laboratory benchtop at ambient temperature (approximately 20° C.). Holograms of the full field-of-view (approximately 16 mm$^2$) were acquired automatically every 30 minutes. Visible division of bacterial micro colonies were detected as early as 60 minutes after the start of image acquisition. Reliably detectable division across most micro colonies in the suspension is achieved approximately 2-3 hours after the start of acquisition for these bacteria. Because detection is based on change over time, presence of debris is not expected to have a significant impact on time-to-detection sensitivity. FIG. 4 shows images obtained by the optical interrogation platform imaging *E. coli* growth over a period of 0 to 180 minutes. FIG. 5 shows images obtained by the optical interrogation platform imaging *E. coli* growth during a period from 240 to 540 minutes.

Time-to-detection highly depends on the optical resolution supported by the system. It is also related to growth media as the experiment used agar phase changed to a gel to contain growth to a particular three-dimensional location in the volume. Hence, tracking of individual micro colonies was not necessary. Thus, the optical interrogation system can be used to detect the presence of growing microorganisms in a biological sample long before traditional methods are capable of doing so. Upon detection of a microorganism present at a very low concentration in a biological sample, the sample may be further tested to determine the identity of the microorganism and its susceptibility to antimicrobial agents.

Additional System Examples

Figure 6:
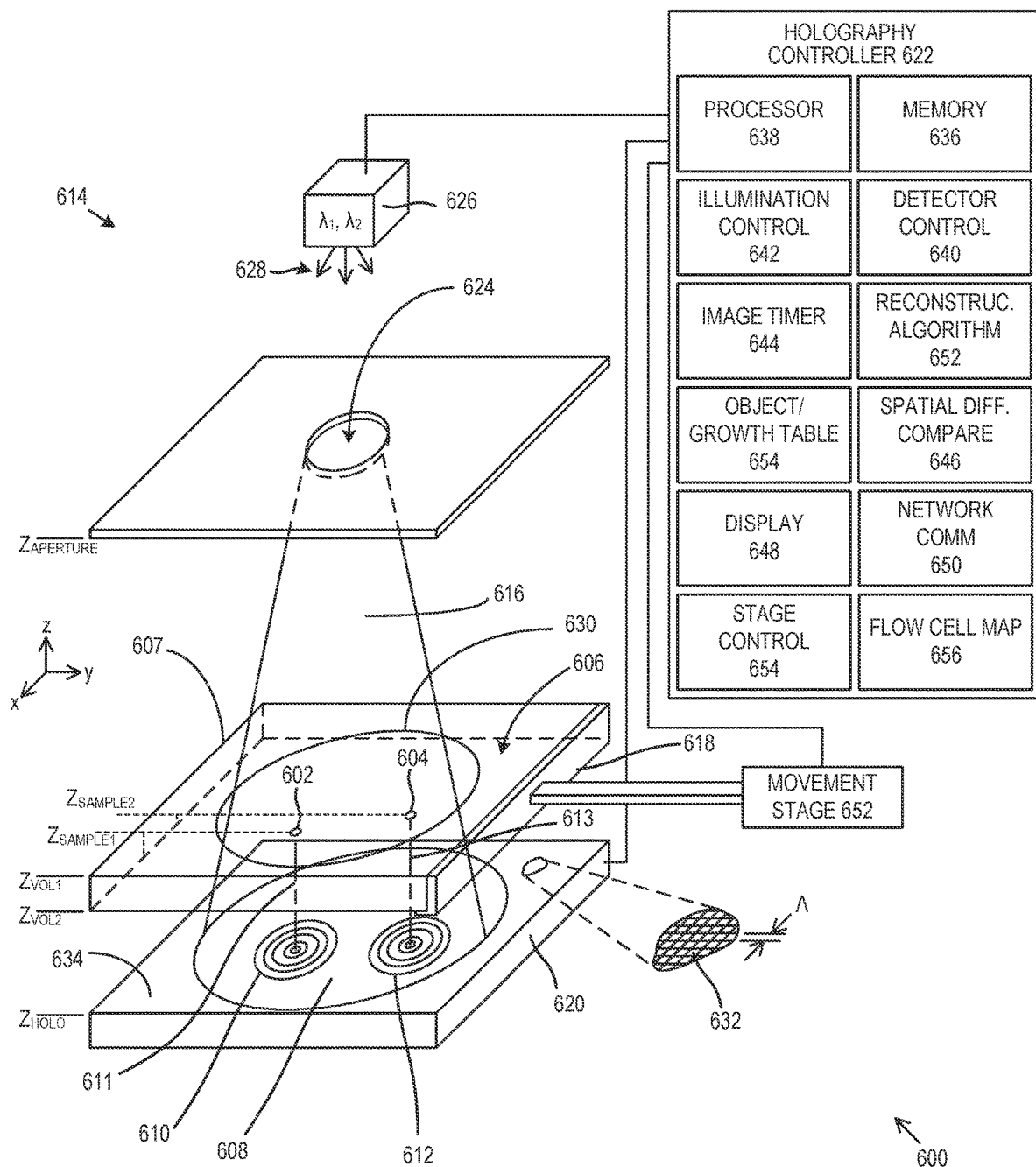
FIG. 6 is a perspective schematic of an example in-line holographic apparatus.

In FIG. 6, an in-line holographic apparatus 600 is situated to determine the presence of microorganisms 602, 604 immobilized or that are free to move in a sample volume 606 of a biological sample container 607. In representative examples, the apparatus 600 can detect a variation over time of an in-line hologram 608 of the sample volume 606, including in an automated fashion, through detection of the sample volume at predetermined times, e.g., during incubation. For example, growth of the microorganisms 602, 604 can produce variation of respective holographic interference patterns 610, 612 of the in-line hologram 608. Variations indicative of the presence of microorganisms 602, 604 can be detected based on time durations associated with microorganism growth rates, such as doubling events, negative growth rates (e.g., rates associated with antimicrobial activity), etc. In typical examples, time durations of doubling events of the immobilized microorganisms 602, 604 are longer than temporal resolutions typically associated with in-line holography, allowing some example systems to provide improved detection, detection over time, imaging, and imaging over time capabilities and lower costs with simpler components and reduced storage and/or processing requirements. In some examples, the in-line hologram 608 can be detected and recorded at rates suitable for detecting doubling events, such as at least twice the doubling rate, or faster, with substantially faster rates possible depending on the detection requirements, such as morphological detection, etc.

In some examples, the in-line holographic apparatus 600 includes a reference beam source 614 situated to direct a reference beam 616 to the sample volume 606, a sample receptacle 618 situated to hold the sample volume 606 in view of the reference beam 616, an optical sensor 620 situated to detect the in-line hologram 608 formed by the reference beam 616 and the sample volume 606, and a holography controller 622 coupled to the optical sensor 620 and configured to determine the variation over time of the in-line hologram 608. The sample volume 606 can include one or more (e.g., a plurality of) sample volume portions corresponding to volumes in microfluidic channels, flow channels, perfusion chambers, etc., of the biological sample container 607 and that can contain biological samples, such as suspended biological samples with microorganisms to be detected, including immobilized microorganisms. In typical examples, the sample receptacle 618 can include a tray or other holding support that receives the biological sample container 607 such that the biological sample can be removable inserted into the in-line holographic apparatus and held by the sample receptacle 618 so that the sample volume 606 can be imaged by the in-line holography apparatus 600. In some examples, the microfluidic channels, flow channels, perfusion chambers, or other parts of the biological sample container 607, can form at least part of the sample receptacle 618.

In representative embodiments, the reference beam source 614 includes a pinhole aperture 624 situated to receive an illumination 628 from an illumination source 626 and the reference beam 616 is directed lens-free from the pinhole aperture 624 to the sample volume 606 and the optical sensor 620. In some examples, the illumination source 626 includes one or more light emitting diodes, laser, or other light source that is situated to produce the illumination 628 with multiple wavelengths that can be used to reduce a twin-image in the hologram 608. In some examples the illumination 628 and the reference beam 616 are incoherent, the illumination 628 and the reference beam 616 are coherent, or the illumination 628 is incoherent and the reference beam 616 is coherent. The shape, diameter, and shape quality (e.g., roughness, ellipticity, etc.) of the pinhole aperture 624 can vary in different embodiments. In typical examples, the pinhole aperture is circular and has a diameter selected in range of 1 μm or smaller, 1 to 10 μm, 10 to 50 μm, 50 to 100 μm, or larger, and together with the wavelength or wavelengths of the illumination 628 determines the numerical aperture of the reference beam 606.

In typical examples, the reference beam 616 diverges to define an imaging area 630 and field of view of the sample volume 606 based on the divergence angle of the reference beam 616 and the distance between a position $Z_{APERTURE}$ of the pinhole aperture 624 and top and bottom plane positions $Z_{VOL1}$, $Z_{VOL2}$ of the sample volume 606. In representative embodiments, the positions $Z_{VOL1}$, $Z_{VOL2}$ are sufficiently proximate each other, i.e., the sample volume 606 is sufficiently thin, in relation to the distance between $Z_{VOL1}$ and $Z_{APERTURE}$ that the positions $Z_{VOL1}$, $Z_{VOL2}$ can be considered effectively one position for purposes of the imaging area 630. In representative examples, the distance $Z_{APERTURE}-Z_{VOL1}$ is selected to be in the range of 40 mm to 100 mm, though distances smaller than 40 mm or greater than 100 mm are also possible. In some examples, the thickness of the sample volume 606 corresponding to the difference $Z_{VOL1}-Z_{VOL2}$ is 2 mm or smaller, 1 mm or smaller, 0.5 mm smaller, etc. Representative imaging areas of the sample volume 606 for a single aperture and reference beam can vary, and can include 50 mm² or larger, 40 mm² or larger, 30 mm² or larger, 20 mm² or larger, 10 mm² or larger, 5 mm² or larger, or smaller than 5 mm², by way of example. In some examples, areas are increased with additional apertures and/or optical sensors. Imaging areas for a single field of view can typically correspond to large volumes, including greater than 2 μL, 5 μL, 10 μL, 20 μL, 50 μL, or greater.

Representative examples of the optical sensor 620 include CMOS or CCD type sensors, that include a plurality of pixels 632 (shown in an expanded cutout) arranged with one or more pixel pitches Λ to form a sensor surface 634 situated to detect the in-line hologram 608. In representative examples, the pitch Λ corresponds to a detector resolution that is sufficiently small to detect the spatial intensity variation of the holographic interference patterns 610, 612 of the in-line hologram 608 or to detect a variation over time of the spatial intensity variation, such as a pitch Λ of 10 μm/pixel, 5 μm/pixel, 2 μm/pixel, 1 μm/pixel, or smaller. In a particular embodiment the pitch Λ is 1.12 μm/pixel. In some examples, the pixel pitch Λ is selected to be sufficiently small to detect spatial intensity characteristics of the in-line hologram 608 that are associated with morphological characteristics of the microorganisms 602, 604. In some examples, characteristics of the reference beam 616 or other components of the in-line holographic apparatus 600 are varied to enhance detection resolution, including varying reference beam wavelength to sample different portions of the pixels 632, varying aperture characteristics such as aperture angles, super-resolution techniques employing relative superposition of sample and illumination, and numerical techniques such as super-resolution via compressed sensing.

In representative examples, the distance between the bottom plane position $Z_{VOL2}$ of the sample volume 606 and the plane position $Z_{HOLO}$ of the sensor surface 634 is 10 mm or smaller, 5 mm or smaller, 2 mm or smaller, etc. In a particular example, the distance $Z_{VOL2}-Z_{HOLO}$ is 4 mm or smaller. In some examples, the distance $Z_{VOL2}-Z_{HOLO}$ is selected so as to provide suitable spatial characteristics for the interference patterns 610, 612 or other interference characteristics of the in-line hologram 608, such as a sufficient propagation distance to produce a corresponding holographic interference between the reference beam 616 and object scattered beams 611, 613. While some examples of the sample volume 606 are generally depicted with a cuboid shape, other shapes can be used, including cylindrical, frustum, elliptoid, etc.

The holography controller 622 includes a detector control 640 and an illumination control 642 respectively in communication with the optical sensor 620 and the illumination source 626 or other light modulation device, such as an optical chopper, light modulator, etc., so that the illumination 628 is provided to form the reference beam 616 and associated hologram 608 that is detected by the optical sensor 620 and so that the optical sensor 620 is ready (e.g., gated, reset, etc.) to detect the hologram 608.

In some examples, the holography controller 622 is a computing device that includes a memory 636 that can include one or more computer readable instructions, such as program modules, that can be executed by at least one processor 638, such as one or more of a microcontroller unit, complex programmable logic device, field programmable gate array, application-specific integrated circuit, programmable logic controller, computer system, etc., arranged singularly or in distributed fashion. Generally, program modules include routines, programs, objects, components, data structures, etc., that perform particular tasks or implement particular abstract data types. Moreover, the disclosed technology may be implemented with other computer system configurations, including hand-held devices, multiprocessor systems, microprocessor-based or programmable consumer electronics, network PCs, minicomputers, mainframe computers, etc.

The memory 636 can includes read only memory (ROM) and random access memory (RAM), one or more storage devices, such as a hard disk drive for reading from and writing to a hard disk, a magnetic disk drive for reading from or writing to a removable magnetic disk, and an optical disk drive for reading from or writing to a removable optical disk (such as a CD-ROM or other optical media). The drives and their associated computer-readable media provide nonvolatile storage of computer-readable instructions, data structures, program modules, and other data for the holography controller 622. Other types of computer-readable media which can store data that is accessible by a PC, such as magnetic cassettes, flash memory cards, digital video disks, CDs, DVDs, RAMs, ROMs, etc., may also be used in the example holographic control environment.

In some examples, a number of program modules can be stored in the memory 636, including an operating system, one or more application programs, other program modules, and program data. In further examples, a user can enter commands and information into the holography controller 622 through one or more input devices, such as a keyboard, and a pointing device, such as a mouse. Other input devices can be included. Thus, in representative examples, the various routines, programs, and program modules can be automated so that biological samples may be received by the in-line holography apparatus 600 so that tests can be performed on the biological samples with little intervention from a user. In some examples, a display device 648 is situated to display images of the hologram 608 or holographic reconstructions of one or more planes of the sample volume 606, including time-lapse images or video recordings associated with microorganism growth or size variation.

An image timer 644 can be used in different examples to synchronize detection and recording of the hologram 608 or associated hologram information in the memory 636 for subsequent comparison or imaging. In some examples, the holography controller 622 includes a spatial difference comparison routine 646 that determines spatial differences associated with holograms recorded at different times, such as by comparing variations of holographic fringes and other spatial frequency encoding features. In some examples, spatial differences can be determined between hologram reconstructions of one or more planes of the sample volume 606 associated with holograms recorded at different times, including area and texture variations of one or more objects, such as the microorganisms 602, 604. Other approaches may include "learning" holographic representation of growth over time with higher-dimensional techniques such as Convolutional Neural Networks and conducting direct inference on observed pixels at each time point of the time-lapse. In representative examples, improved microorganism detectability is achieved for the sample volume 606 based on the immobilized but growing (or declining) microorganisms and background immobilized objects that have spatial characteristics that do not vary over time. For example, in comparing spatial differences, a substantial set of the background objects and associated signal characteristics can be eliminated through image subtraction so as to improve a signal to noise ratio for the spatial difference comparison routine 646.

In some examples, the holography controller 622 includes a numerical reconstruction routine 652 that is configured to reconstruct one or more planes of the sample volume 606 associated with the microorganisms 602, 604 based on the hologram 608 detected at the plane $Z_{HOLO}$ of the optical sensor 620. In general, such routines approximate solutions to Fresnel-Kirchoff diffraction integral by employing a Fresnel approximation (Fresnel integral) or a convolutional approach at any focal plane between $Z_{VOL1}$ and $Z_{VOL2}$, followed by intensity and phase extraction. In some examples, the numerical reconstruction routine 652 includes a Gerchberg-Saxton algorithm. Objects, such as the microorganisms 602, 604, that are identified can be tracked in an object growth table 654 for comparison with holograms detected at later times to determine if a spatial variation occurs that is associated with the presence of the microorganisms 602, 604.

The disclosed technology may also be practiced in distributed computing environments where tasks are performed by remote processing devices that are linked through a communications network. In a distributed computing environment, program modules may be located in both local and remote memory storage devices. For example, holographic comparison by the holography controller 622 associated with an indication as to the presence of the microorganisms 602, 604, immobilized or motile, in the sample volume 606 can be performed locally upon receiving a plurality of holograms for comparison or can also be performed remotely in space and/or time from the detection of holograms by the optical sensor 620. In some examples, the holography controller includes a network communication connections 650 to communicate with external device or other computers, e.g., through a local area network (LAN) or wide area network (WAN). The in-line holographic apparatus 600 can further include a movement stage 652 coupled to the sample volume 606, such as through a side of the sample receptacle 618, though it will be appreciated that various couplings can be used to provide translational and/or rotational movement of the sample volume 606. The controller 622 can include a stage control 654 that can command and cause movement of the sample receptacle 618 to different positions, e.g., based on a flow cell map 656, so that different flow cells or portions of a flow cell can be aligned in view of the reference beam 616 and interrogated, e.g., between the reference beam source 614 and the optical sensor 620. In representative examples, a movement stage 652 can be omitted.

Figure 7:
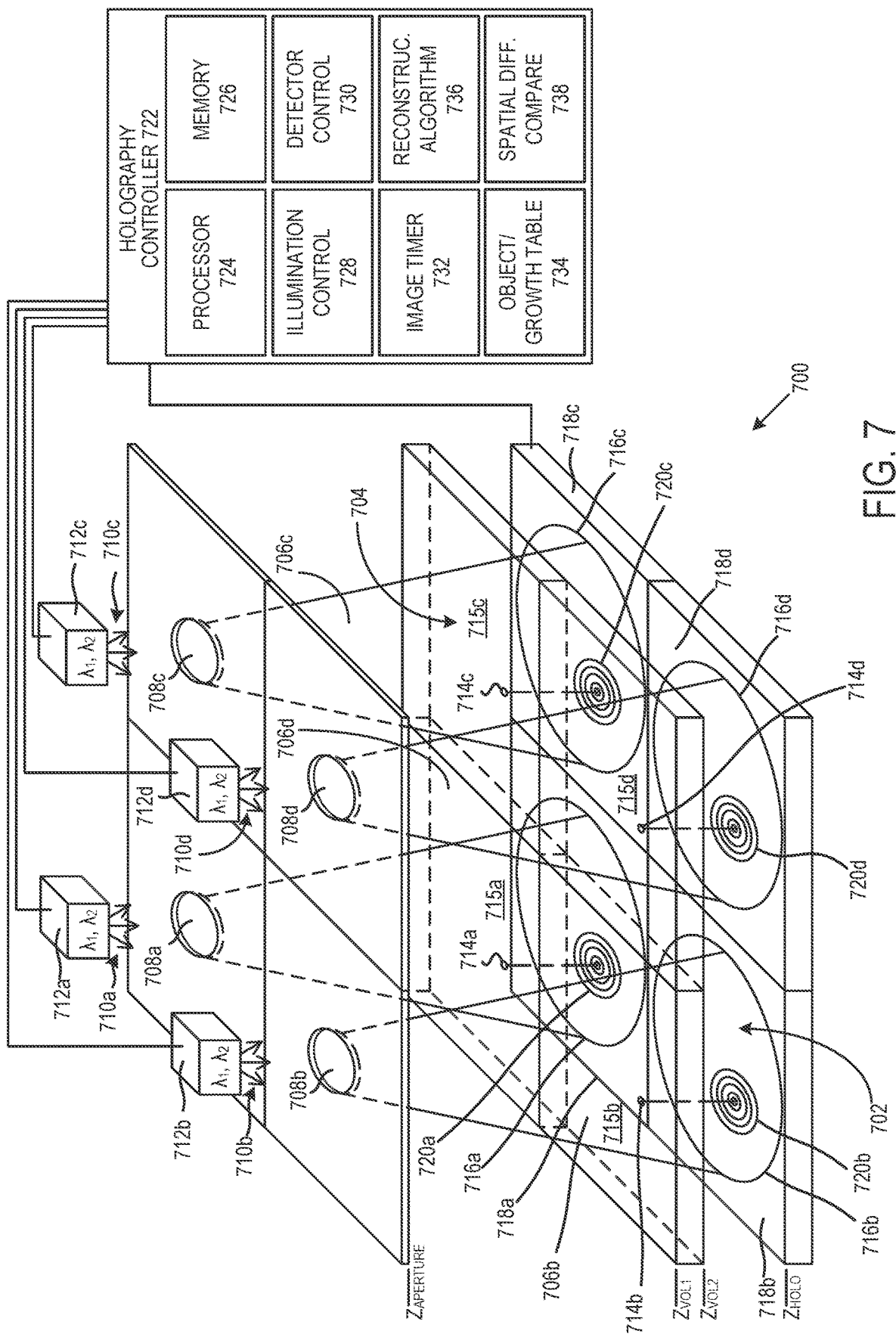
FIG. 7 is a perspective schematic of an example mosaicked in-line holographic apparatus.

FIG. 7 shows an example in-line holographic apparatus 700 that has a mosaicked field of view 702 of a sample volume 704 with a plurality of reference beams 706a-706d emitted from respective pinhole apertures 708a-708d based on respective illuminations 710a-710d (typically multi-wavelength) received from respective illumination sources 712a-712d. In some examples, a single illumination source can be used to illuminate the pinhole apertures 708a-708d, and in other examples other quantities of illumination sources can be used. In particular examples, a pinhole aperture 708a can include a plurality of spaced apart pinhole apertures, typically at a small distance (e.g., less than about 1 mm), and the illumination source 708a can include separate illumination sub-sources emitting at separate respective wavelengths and coupled to the respective spaced apart pinhole apertures. Alternatively, each spaced apart pinhole aperture can be coupled to a respective wavelength filter so that reference subbeams at different wavelengths are emitted from the respective spaced apart pinhole apertures. The other pinhole apertures 708b-708d and illumination sources 712b-712d can be similarly configured and detected holograms can be registered with respect to each other based on subsampling of the respective optical sensor portions 718a-718d.

The sample volume 704 typically includes a suspended biological sample having immobilized or motile microorganisms 714a-714d in respective sample volume portions 715a-715d. Sample containers and sample receptacles are omitted for clarity and convenience of illustration though it will be appreciated that various containers and receptacles for supporting and manipulating biological samples can be used. Respective in-line holograms 716a-716d are formed and detected, including holographic pattern features 720a-720d that are generated based on the immobilized or mobile microorganisms 714a-714d, with the different optical sensor portions 718a-718d. In some examples, the optical sensor portions 718a-718d can form a single sensor or multiple sensors. In some mosaic embodiments, at least one of the sample volume portions 715a-715d is used as a growth control and one or more others of the sample volume portions 715a-715d include selective media or antimicrobial agents. In further mosaic embodiments, the sample volume portions 715a-715d are not isolated from each other and the multiple reference beams 706a-706d effectively increase the imaging area of the in-line holographic apparatus 700. In some examples, the reference beams 706a-706d have respective imaging areas that can overlap at the sample volume 704 so that the mosaicked field of view 702 can have continuous coverage over at least a portion of the sample volume 704 including all of the sample volume 704 in selected examples. The sample volume can be relatively large, with some examples have a volume of 0.01 mL or greater, 0.05 mL or greater, 0.1 mL or greater, 0.5 mL or greater, or 1 mL or greater, etc.

The in-line holographic apparatus 700 can include a holography controller 722 that can control holographic imaging and holographic imaging over time of the sample volume 704. The holography controller typically includes at least one processor 724, and a memory 726 that includes stored instructions associated with the detection of the holograms 716a-716d. In representative examples, the holography controller 722 includes an illumination control 728 that can cause the illumination sources 712a-712d to generate the illuminations 710a-710d at respective times or periods that can be the same or different from each other, and can be controlled based on an image timer 732. In representative examples, the hologram controller 722 includes a detector control 730 in communication with the optical sensor portions 718a-718d so as to receive one or more hologram signals associated with the holograms 716a-716d. In some examples, objects are detected, such as the microorganisms 714a-714d, and monitored over time, e.g., in an object growth table 734, so as to determine the presence of the microorganisms 714a-714d, or other characteristics, such as morphological characteristics, microorganism quantity or concentration, growth control characteristics, antimicrobial responsiveness, selective media based species determination, etc., depending on the particular application. In some examples, objects and object variations (e.g., growth), can be determined with a spatial differences comparison routine 738 that compares spatial variations within the holograms 716a-716d, within reconstructions of the sample volume portions 715a-715d based on the holograms 716a-716d and one or more reconstruction algorithms 736, or spatial variations over time of holograms or reconstructions. In some examples, one or more displays are included to show holographic information, amplitude and/or phase features, reconstructed sample volume features, sample volume feature variation over time (e.g., microorganism growth or decline), etc. Some examples can include one or more communications modules for remote communication. Selected examples can include a movement stage (not shown) to move the sample volume.

Figure 8:
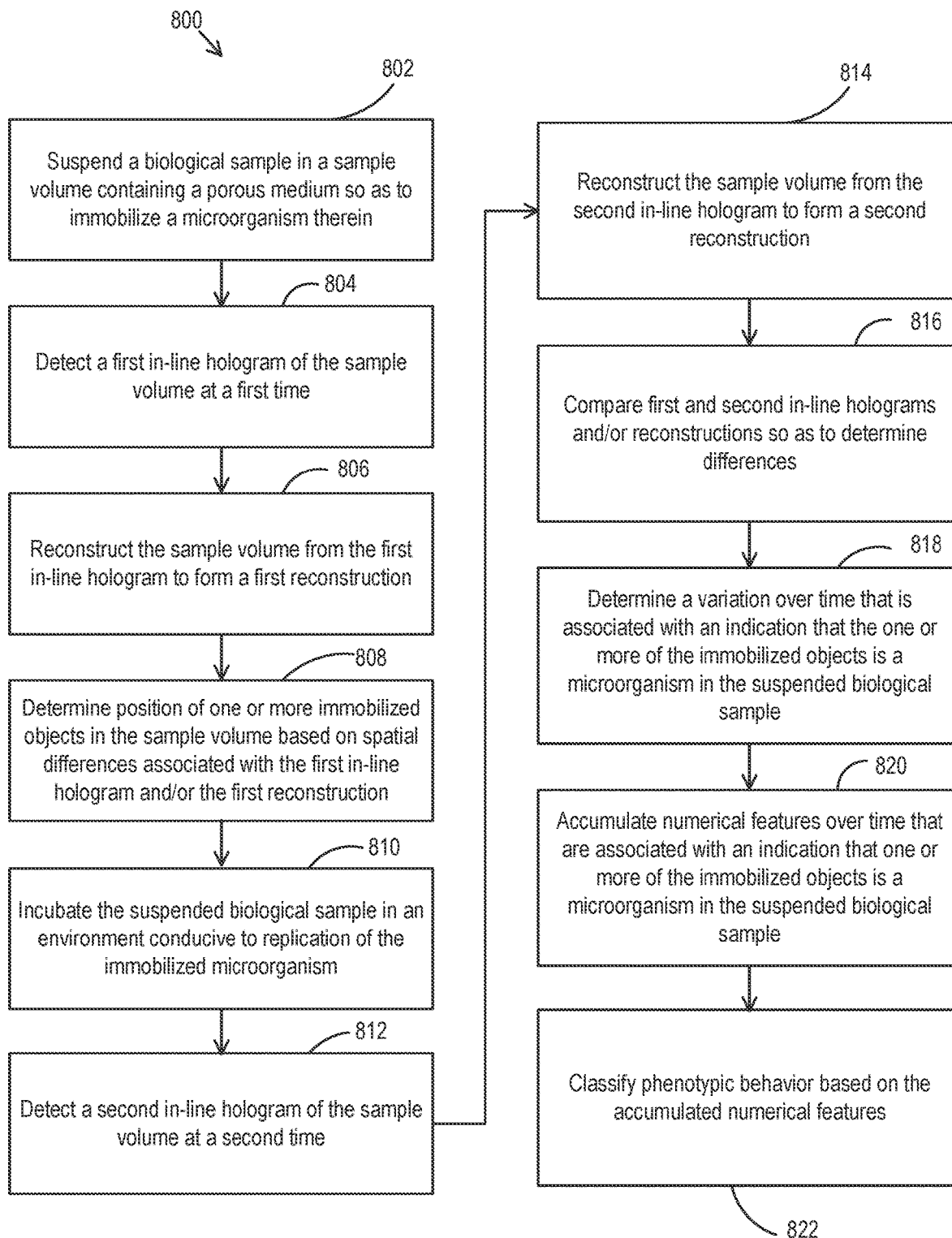
FIGS. 8-12 are flowcharts of example holography methods.

FIG. 8 depicts an example method 800 for detecting the presence of a microorganism. At 804, a first in-line hologram of a sample volume is detected at a first time, and at 812, a second in-line hologram of the sample volume is detected at a second time. At 818, a variation over time associated with the in-line holograms is determined (e.g., between the first and second in-line holograms) that is associated with an indication that one or more objects immobilized in the sample volume is a microorganism. In some examples, at 802, the sample volume includes a biological sample that includes microorganisms suspended in a porous medium so as to immobilize the microorganisms to be detected. In some examples, at 806, the spatial characteristics of objects in the sample volume are reconstructed from the first in-line hologram, forming a first reconstruction of the sample volume.

Reconstructions can be performed according to various methods, such as with various diffraction propagation approximations (e.g., Fresnel approximation) and iterative phase retrieval approaches, such as Gerchberg-Saxton algorithms. The in-line holograms are generated as a reference beam interacts with the sample volume and produces a complex interference pattern based on object beams that are formed from optical interaction between the reference beam and the immobilized objects and resulting interference between the reference beam and object beams. Phase components associated with the immobilized objects is extracted from the intensity characteristics of the hologram. In typical examples, a Fresnel integral is applied to the hologram intensity to determine a plane associated with an immobilized object and an iterative Gerchberg-Saxton algorithm is used to reconstruct intensity and phase of the immobilized object.

In some examples, at 808, the reconstructions allow a determination of the position (e.g., a z-position, an x-y position, an x-y-z position, etc.) of one or more of the objects immobilized in the sample volume based on spatial differences of the first in-line hologram or the first reconstruction. In typical examples, at 810, the suspended biological sample is incubated in an environment conducive to microorganism replication. At 814, in some examples, spatial characteristics of the sample volume are reconstructed from the second in-line hologram detected at a later time, sometimes selected in relation to a suitable microorganism division rate or other biological rate. In representative examples, at 816, the first in-line hologram and the second in-line hologram, and/or the reconstructions of the first in-line hologram and the second in-line hologram, are compared so as to identify holographic and/or reconstructed spatial differences, so that the variations over time can be determined at 818. In some examples, growth detection is performed without reconstructing the precise position and/or plane of the immobilized object, or without performing reconstruction at every holographic detection event. Various examples herein can use the linearity of optical transforms associated with reconstruction and manipulate holographic information (e.g., add, subtract, etc.) without loss of information. Additionally, intensity variation of the holograms over time (e.g., spatial intensity variation) can be used to determine microorganism presence. In typical examples, at 820, multiple holograms can be obtained so that numerical features of the detected objects can be accumulated over time. The accumulated features can be associated with an indication that one or more of the immobilized objects corresponds to a microorganism in the suspended biological sample. In some examples, at 822, the phenotypic behavior of an object can be classified based on the accumulated numerical features, such as growth, death, lysis, filamentation, debris, etc.

Figure 9:
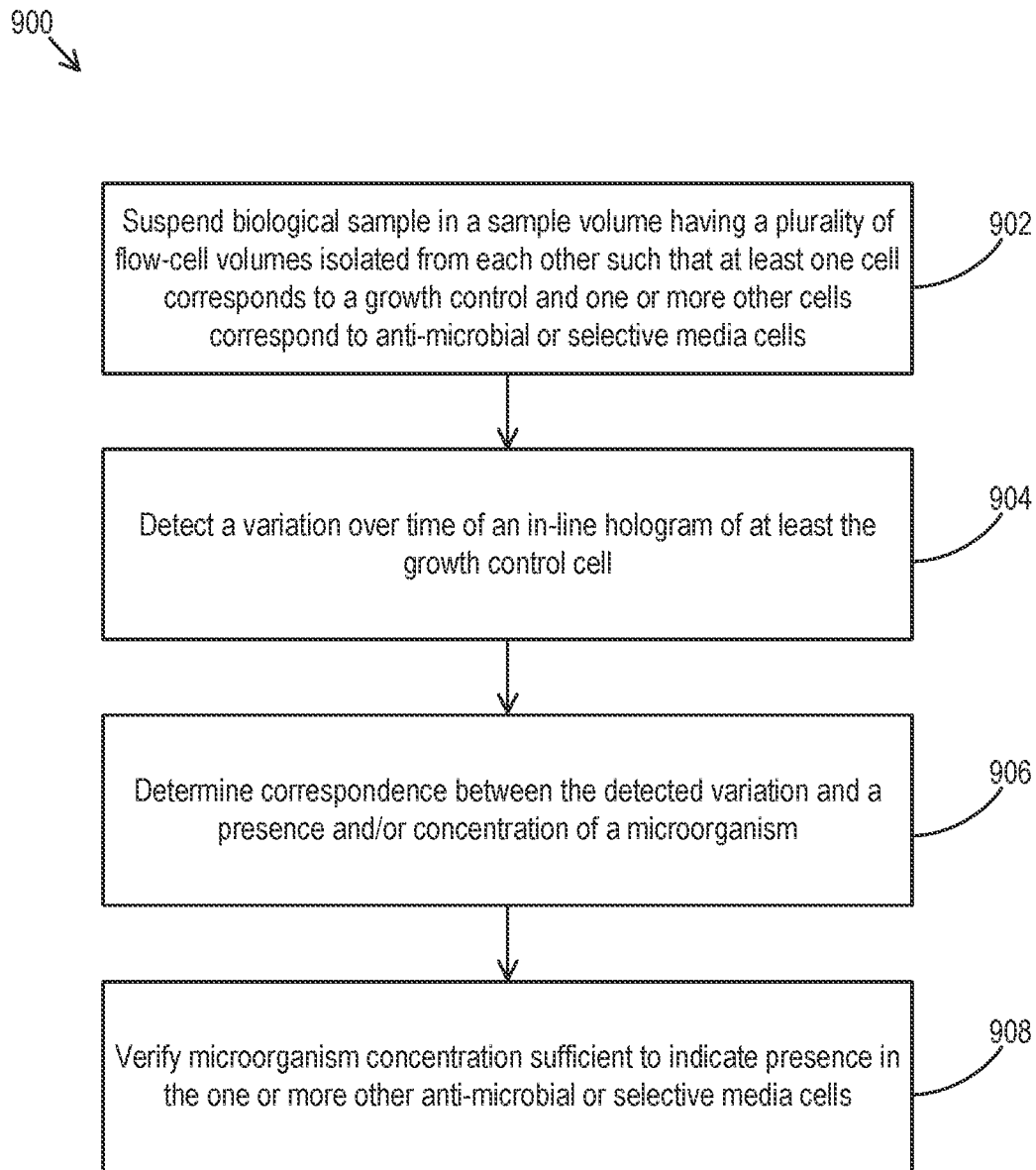

FIG. 9 shows an example method 900 that includes, at 902, suspending a biological sample in a sample volume having a plurality of flow-cell volumes isolated from each other such that at least one cell corresponds to a growth control and one or more other cells correspond to anti-microbial or selective media cells. At 904, a variation over time of an in-line hologram of at least the growth control cell is detected. At 906, a correspondence between the detected variation and a presence and/or concentration of a microorganism in the growth control cell is determined. At 908, a microorganism concentration sufficient to indicate a presence in the one or more other anti-microbial or selective media cells is determined.

Figure 10:
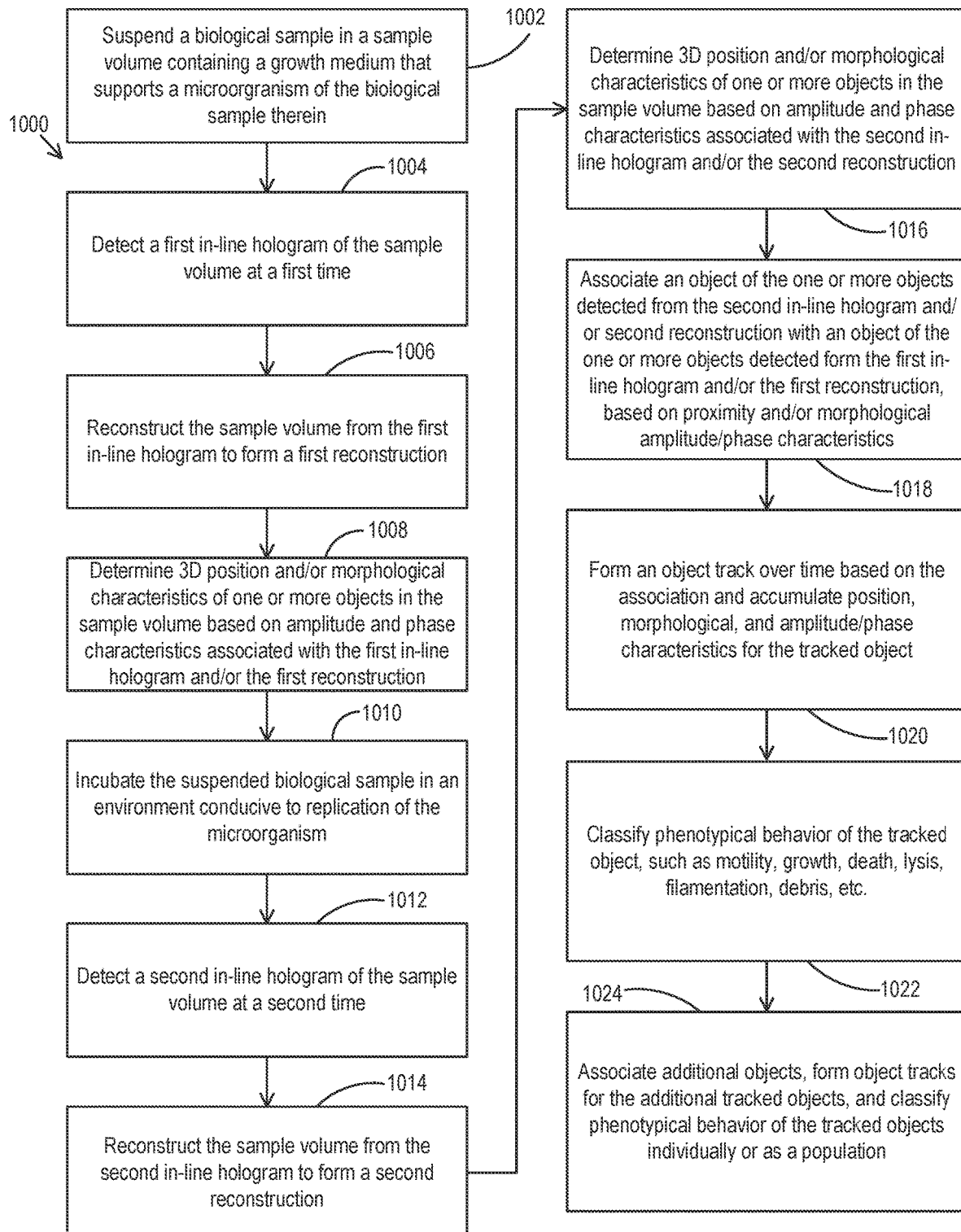

FIG. 10 is an example method 1000 that includes, at 1002, suspending a biological sample in a sample volume containing a growth medium supporting a microorganism of the biological sample therein. In representative examples, the supporting growth medium allows the microorganism to move within the sample volume, though the microorganism can also be immobilized by the supporting growth medium. At 1004, an automated in-line holographic apparatus that typically directs an illumination beam lenslessly from a pin-hole aperture through the sample volume to an optical detector, detects a first in-line hologram of the sample volume at an initial time (e.g., at a beginning of a test or at a selected time or sequence point during the test). At 1006, the 3D spatial characteristics of the sample volume are reconstructed from the first in-line hologram, so as to form a first hologram reconstruction. Various techniques can be used for hologram reconstruction, diffraction theory (e.g., iterative Gerchberg-Saxton), and/or deep learning (e.g., convolutional neural networks). For example, in deep learning approaches, such as convolutional neural networks, the network layers can be supervised and the network activations can be trained to map raw hologram (interferometric) space into in-focus image plane at a specified focal distance.

In selected examples, hologram reconstruction processes can include pre-processing of detected hologram data. For example, multi-wavelength hologram registration can be used where multiple pinhole apertures are physically separated by less than about 1 mm to form fixed predetermined offsets, such as with multiple wavelengths directed to a common sample volume or sample volume portion through the respective proximate apertures. The pixel grid of the optical detector subsampled with the multiple wavelengths, and the acquired image data is shifted relative to each other on an upsampled grid such that the relative offsets are eliminated. De-noising of the detected hologram data can be provided with deep learning approaches (such as convolutional neural networks) or deconvolution of an estimated/theoretical Point Spread Function (PSF) in 2D or volumetric PSF in 3D. For example, de-noising with convolutional neural networks can remove or suppress imaging sensor non-uniformities (e.g. pixel response non-uniformity or striping), an image degradation of the optical system (e.g. PSF), and diffraction ring cross-talk interference, including without formulating analytical models for corresponding sources of noise. In convolutional neural network examples, the network layers are typically trained using one or more suboptimally acquired holograms (single-wavelength/single-aperture or numerically degraded) where target data is a higher fidelity hologram (multi-wavelength/multi-aperture, multi-sampled/averaged). The corresponding trained network can then be applied to both lower-fidelity holograms as well as higher-fidelity holograms to suppress various noise contributions, such as those described above. In some examples, in a manner similar to PSF deconvolution in optical (e.g., confocal) microscopy, PSF of a lens-free holographic system can be established either empirically (e.g., by recording a signal associated with particles below a resolution limit) or analytically. Techniques such as Richardson-Lucy algorithm can then be employed to deconvolve (or "take out") the PSF from the image data. The principal difference is that in lens-free imaging the above procedure can be applied directly to a raw hologram (i.e., before reconstruction). By pre-processing the detected hologram data, the de-noising and/or deconvolution can improve volumetric position estimation accuracy as well as amplitude and phase representation of small spherical objects that approximate point sources. Such approximations can be particularly applicable and valid for individual and/or clustered bacteria.

At 1008, from the sample volume reconstruction, a 3D position of one or more objects in the sample volume (typically many objects in biological sample volumes) and/or morphological characteristics of the one or more objects in the sample volume can be determined, based on amplitude and phase characteristics associated with the first in-line hologram and/or first reconstruction. The suspended biological sample is typically incubated in an environment conducive to microorganism replication, at 1010, for a predetermined time period. In representative examples, multiple holograms are detected in a test run at different points in time, and the time intervals need not be identical. Time resolution and time interval variation can be selected based on incubation characteristics, growth media, microorganism growth stages, etc. At 1012, a second in-line hologram is detected at a second time. The second in-line hologram is reconstructed at 1014, and can use one or more techniques that were used in the reconstructions of the first in-line hologram.

At 1016, a 3D position of one or more objects in the sample volume and/or morphological characteristics of the one or more objects in the sample volume can be determined, based on amplitude and phase characteristics associated with the second in-line hologram and/or second reconstruction. In some examples, detected hologram data or respective reconstructions can be compared over time to determine object locations and characteristics by analyzing differential variations on a spatial (or per-pixel) basis. Deep learning approaches based on Bayesian statistical inference, including convolutional neural networks, can also be employed to recognize and quantify variation patterns arising from differential holograms or differential reconstructed images. In convolutional neural network examples, the network is trained in a supervised fashion to recognize variational spatial patterns due to, by way of example, multiple species of bacteria and fungus versus other biological or non-biological particles.

Because the objects detected with the first hologram may grow, die, move, or provide other microorganism signatures that vary over the time interval between the first and second hologram detections, objects detected at 1016 may be closely related to objects detected in the first in-line hologram. In some examples, at 1018, an object of the one or more objects detected from the second in-line hologram and/or second reconstruction is associated with an object of the one or more objects detected from the first in-line hologram and/or the first reconstruction, based on proximity and/or morphological amplitude/phase characteristics. In some immobilized sample volume examples, object associations can be omitted or relaxed as the object does not change position (though growth, death, and/or other morphological characteristics may change) between first and second hologram detections due to the immobilizing growth medium. At 1020, an object track for the associated objects can be created over time to accumulate position, morphological, and amplitude/phase characteristics for the tracked object. Object tracks can be 1D, 2D, and/or 3D in some examples. In selected immobilized examples, object tracks can be omitted. In some examples (and particularly convenient in immobilized examples), numerical features of a detected object can be accumulated over time that are associated with an indication that the immobilized object is a microorganism suspended in the biological sample volume. At 1022, phenotypical behavior of the tracked object can be classified, such as object motility, growth, death, lysis, filamentation, debris, etc. At 1024, additional objects can be associated, object tracks formed for the additional tracked objects, and phenotypical behavior of the tracked objects classified, individually or as a population. In selected immobilized examples, motility can be omitted. In either mobilized or immobilized examples, based on the resolution of the apparatus (e.g., resolving 10 µm, 5 µm, 1 µm, or 0.5 µm dimension of the sample volume, for relative large fields of view) and the ability to identify individual objects, actual object quantities and corresponding volumetric concentrations in the sample volume can be determined, including individual cells or populations of cells.

Figure 11:
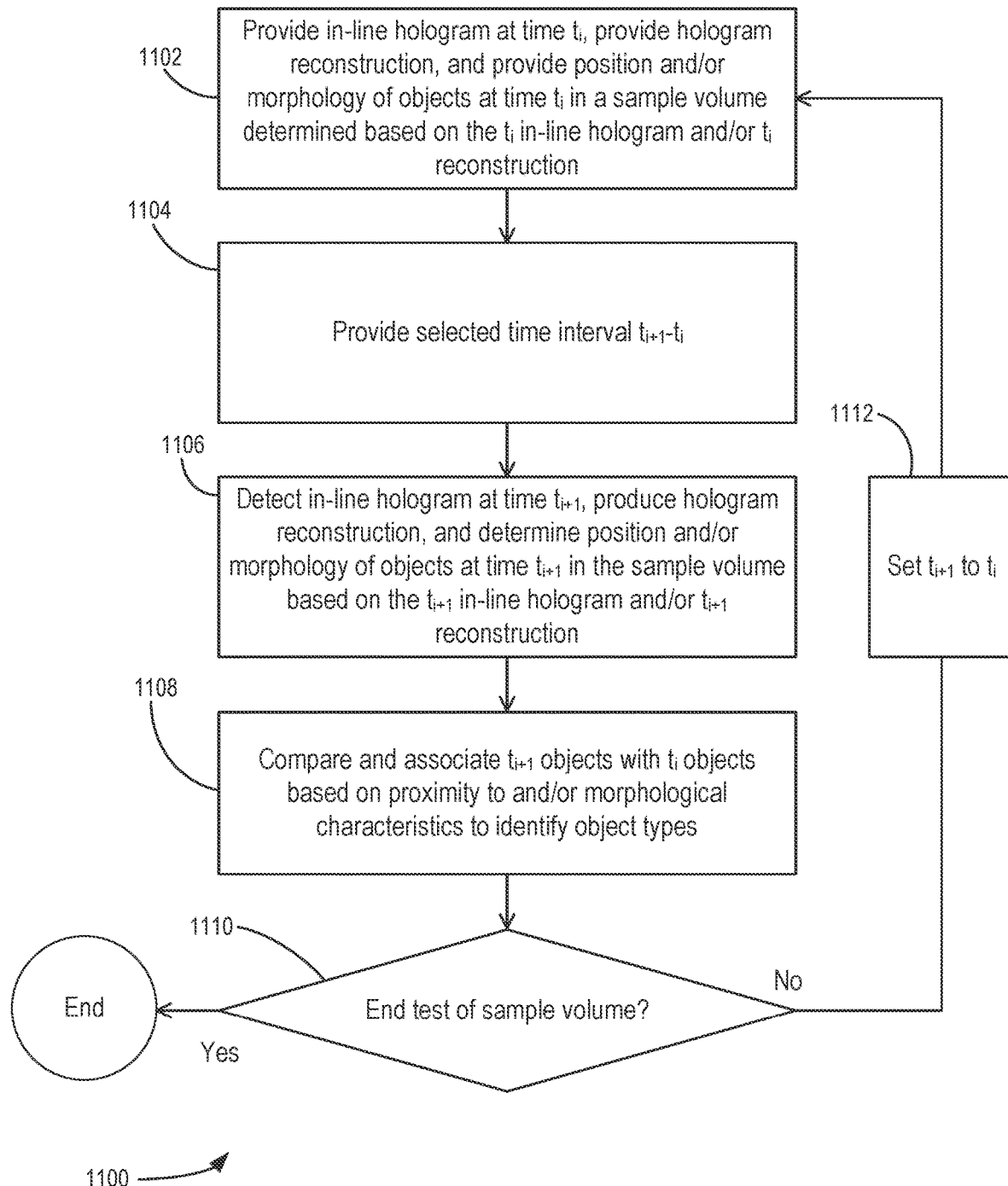

FIG. 11 is an example iterative object association method 1100 in the testing a sample volume that can contain a microorganism to be detected. At 1102, an in-line hologram is provided of time $t_i$, a corresponding hologram reconstruction can be provided, and position and/or morphology of objects at time $t_i$ in the sample volume are provided that are determined based on the $t_i$ in-line hologram and/or $t_i$ reconstruction. For example, if $t_i$ corresponds to a first in-line hologram of a series of holograms for a test of the sample volume, then the in-line hologram can be produced and detected at the time $t_i$, the sample volume reconstructed, and/or object positions determined rather than, e.g., being provided in another way, such as through access from a local or remote data storage. At 1104, a selected time interval $t_{i+1}-t_i$ is provided after the time $t_i$. At 1106, an in-line hologram is detected at time a corresponding hologram reconstruction is produced, and position and/or morphology of objects at time $t_{i+1}$ in the sample volume are determined based on the $t_{i+1}$ in-line hologram and/or $t_{i+1}$ hologram reconstruction. The $t_{i+1}$ objects with $t_i$ objects are compared and associated at 1108 based on proximity to and/or morphological characteristics to identify object types. At 1110, a check is performed as to whether the in-line hologram imaging test of the sample is complete for the sample volume. If the test is not yet complete, the time $t_{i+1}$ can be set to a time $t_i$ and the process of providing an in-line hologram at 1102 (which can correspond to the in-line hologram provided in the previous step 1106) can be repeated. In representative examples, object associations can be updated, revised, including with new object associations, as subsequent holograms are obtained, analyzed, and compared with previous hologram, sequences of holograms, and/or object association histories. Multiple objects in a sample volume can be associated and identified and thereby quantified. Based on the size of the sample volume and the ability to quantify the multiple objects within the sample volume at different growth stages, precise object concentrations (including for different object types or taxa) can be determined.

Figure 12:
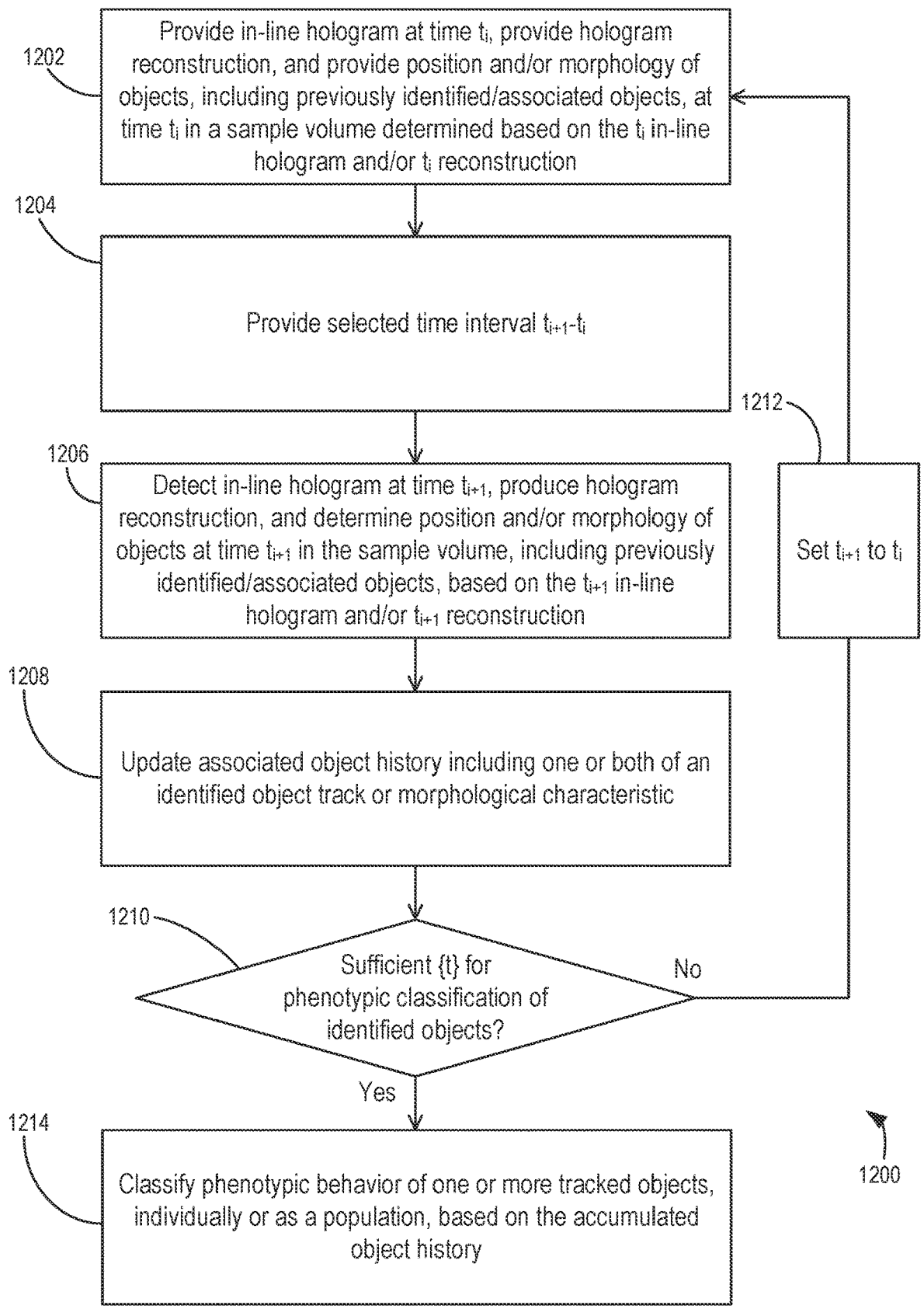

FIG. 12 is an example of an iterative phenotype classification method 1200 that can be used in testing a biological sample in a sample volume with an automated in-line holography apparatus. At 1202, an in-line hologram is provided of time $t_i$, a corresponding hologram reconstruction can be provided, and position and/or morphology of objects at time $t_i$ in the sample volume are provided that are determined based on the $t_i$ in-line hologram and/or $t_i$ reconstruction. For example, if t corresponds to a first in-line hologram of a series of holograms for a test of the sample volume, then the in-line hologram can be produced and detected at the time $t_i$, the sample volume reconstructed, and/or object positions determined rather than, e.g., being provided in another way, such as through access from a local or remote data storage. At 1204, a selected time interval $t_{i+1}-t_i$ is provided after the time $t_i$. At 1206, an in-line hologram is detected at the time $t_{i+1}$, a corresponding hologram reconstruction is produced, and position and/or morphology of objects at time $t_{i+1}$ in the sample volume, including previously identified and associated objects in the sample volume or previously associated objects (e.g., that move, grow, die, etc.), are determined based on the $t_{i+1}$ in-line hologram and/or $t_{i+1}$ hologram reconstruction. In typical examples, objects are identified and object associations are formed after a plurality of holographic samples in a time sequence of the test. At 1208, an object history of an associated object (e.g., an object that changes position in the sample volume through flagellation, or a bacterial growth, splitting, including individual or populations, etc.) can be updated, e.g., in computer memory, based on changes of detected or computed object parameters, such as an object track (e.g., a movement path, a centroid position change of a population, filamentation direction, etc.) or morphological characteristics (e.g., shape, microorganism features, patterns, colors, size, etc.). In some examples, objects can be compared between times time $t_{i+1}$ and object associations produced or updated, similar to as shown in the example method 1100. At 1210, a check is performed as to whether the set of hologram events is sufficient (e.g., sufficient number of events and/or a sufficient duration for incubation, etc.) to support a phenotypic classification of the identified objects based on the object histories. If a sufficient set of in-line hologram events has not yet been collected, the time $t_{i+1}$ can be set to a time $t_i$ and the process of providing an in-line hologram at 1202 (which can correspond to the in-line hologram provided in the previous step 1206) can be repeated. If the set of events is sufficient, at 1214, phenotypic behavior of one or more of the identified objects, individually or as a population, is classified based on the accumulated object history for the object. In some examples, such classifications can be updated, revised (including being replaced), as additional holograms in a test sequence are detected. Classification of numerical features that represent phenotypic behavior over time for an identified object can be accomplished with various techniques, such as, but not limited to, regression, discriminant analysis, decision trees, and/or neural networks (e.g. convolutional neural networks). Classification categories can include (but are not limited to) object motility, growth, death, lysis, filamentation, and debris. Detected objects that exhibit response that can be representative of bacterial phenotypic response can be selected for further analysis along with their respective measured features. Such analyses can be performed on an individual object basis as well as population basis.

Figure 13:
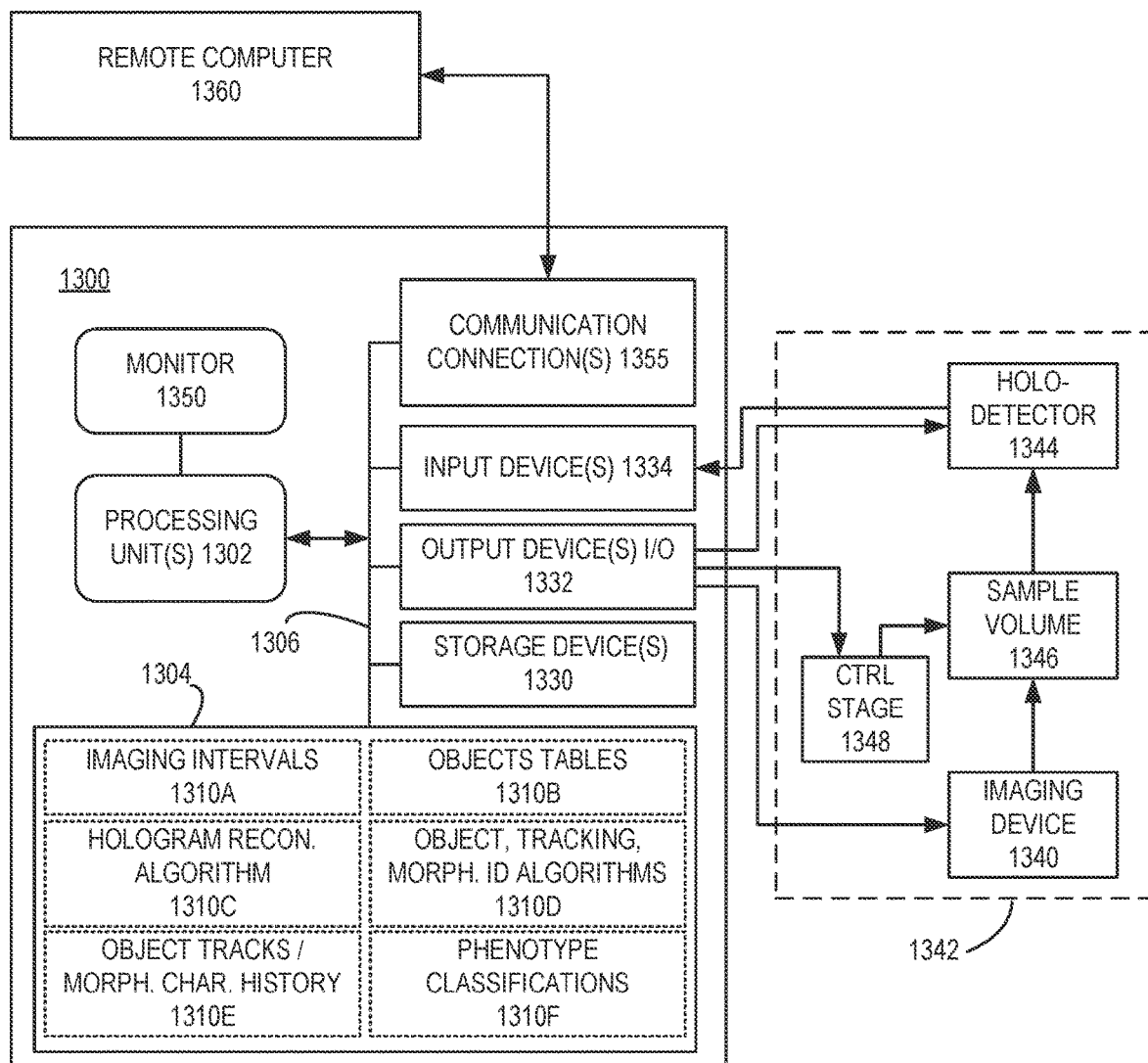
FIG. 13 is a schematic of an example computing environment.

FIG. 13 and the following discussion are intended to provide a brief, general description of an exemplary computing environment in which the disclosed technology may be implemented. Although not required, the disclosed technology is described in the general context of computer-executable instructions, such as program modules, being executed by a computing unit, dedicated processor, or other digital processing system or programmable logic device. Generally, program modules include routines, programs, objects, components, data structures, etc., that perform particular tasks or implement particular abstract data types. Moreover, the disclosed technology may be implemented with other computer system configurations, including hand-held devices, multiprocessor systems, microprocessor-based or programmable consumer electronics, network PCs, minicomputers, mainframe computers, dedicated processors, MCUs, PLCs, ASICs, FPGAs, CPLDs, systems on a chip, and the like. The disclosed technology may also be practiced in distributed computing environments where tasks are performed by remote processing devices that are linked through a communications network. In a distributed computing environment, program modules may be located in both local and remote memory storage devices.

With reference to FIG. 13, an exemplary system for implementing the disclosed technology includes a computing device 1300 that includes one or more processing units 1302, a memory 1304, and a system bus 1306 that couples various system components including the system memory 1304 to the one or more processing units 1302. The system bus 1306 may be any of several types of bus structures including a memory bus or memory controller, a peripheral bus, and a local bus using any of a variety of bus architectures. The memory 1304 can include various types, including volatile memory (e.g., registers, cache, RAM), non-volatile memory (e.g., ROM, EEPROM, flash memory, etc.), or a combination of volatile and non-volatile memory. The memory 1304 is generally accessible by the processing unit 1302 and can store software in the form computer-executable instructions that can be executed by the one or more processing units 1302 coupled to the memory 1304. In some examples, processing units can be configured based on RISC or CSIC architectures, and can include one or more general purpose central processing units, application specific integrated circuits, graphics or co-processing units or other processors. In some examples, multiple core groupings of computing components can be distributed among system modules, and various modules of software can be implemented separately.

The exemplary computing device 1300 further includes one or more storage devices 1330 such as a hard disk drive for reading from and writing to a hard disk, a magnetic disk drive for reading from or writing to a removable magnetic disk, and an optical disk drive for reading from or writing to a removable optical disk (such as a CD-ROM or other optical media). Such storage devices can be connected to the system bus 1306 by a hard disk drive interface, a magnetic disk drive interface, and an optical drive interface, respectively. The drives and their associated computer-readable media provide nonvolatile storage of computer-readable instructions, data structures, program modules, and other data for the computing device 1300. Other types of non-transitory computer-readable media which can store data that is accessible by a PC, such as magnetic cassettes, flash memory cards, digital video disks, CDs, DVDs, RAMs, ROMs, and the like, may also be used in the exemplary computing environment. The storage 1330 can be removable or non-removable and can be used to store information in a non-transitory way and which can be accessed within the computing environment.

As shown in FIG. 13, the computing device 1300 is coupled to an output device I/O 1332 so that suitable output signals (e.g., digital control voltage and/or current signals) are provided to imaging devices 1340 of an in-line holography generator 1342. The imaging devices 1340 typically include illumination sources generating light at one or more wavelengths and pinhole apertures to receive the illumination and lenslessly direct the illumination to a sample volume 1346. A hologram is formed at a hologram detector 1344. Input device I/O 1334 is coupled to the bus 1306 so that data signals and/or values corresponding to in-line holograms detected with the detector 1344 can be stored in the memory 1304 and/or storage 1330 and/or processed with the processing unit 1302. In some examples, a control stage 1348, such as a translation and/or rotation stage, can be coupled to the sample volume (and/or the detector 1344 and imaging device 1340) so that relative movement between the sample volume 1346 and illumination/detection beams can be produced. The control stage 1348 can provide a translation so that different cells for the sample volume 1346, e.g., for large sample volumes, can be illuminated and detected at different times.

In representative examples, the detected holograms are used to reconstruct the 3D physical characteristics of the sample volume 1346, so that immobilized or mobile objects in the sample volume 1346 (such as microorganisms) can be detected. Imaging and/or detection intervals, gating, synchronization, etc., can be stored in a memory 1310A along with various data tables for storing detected hologram data, manipulated data (e.g., holographic reconstructions), and algorithms for analyzing data. For example, identified/associated objects (e.g., a moving microorganism, a growing bacterial colony, etc.) and unassociated or static objects can be stored in objects tables 1310B. Hologram reconstruction algorithms, such as Gerchberg-Saxton (GS) and/or Bayesian deep learning methods, can be stored in a memory 1310C. Object identification, object tracking, and/or morphological identification algorithms, such as convolutional neural networks, can be stored in a memory 1310D. As objects are tracked and associated morphological characteristics detected, histories of object characteristics can be stored in a memory 1310E. Phenotype classifications that can be determined based on the object tracks and morphological characteristics can be stored in a memory 1310F.

A number of program modules (or data) may be stored in the storage devices 1330 including an operating system, one or more application programs, other program modules, and program data. A user may enter commands and information into the computing device 1300 through one or more input devices such as a keyboard and a pointing device such as a mouse. Various other input devices can be used as well. These and other input devices are often connected to the one or more processing units 1302 through a serial port interface that is coupled to the system bus 1306, but may be connected by other interfaces such as a parallel port, game port, or universal serial bus (USB). In representative examples, the various routines, programs, and program modules can be automated so that biological samples may be received by the in-line holography generator 1342. The in-line holography generator 1342 can include or be coupled to the computing device 1300 so that tests can be performed on the biological samples with little intervention from a user. A monitor 1350 or other type of display device is also connected to the system bus 1306 via an interface, such as a video adapter. The monitor 1350 can be used to display hologram images, reconstructed sample volume images in 2D or 3D (e.g., perspective images, focal planes, z-planes, etc.), time lapse images of growth, images with static objects and/or debris subtracted, etc. Some or all data and instructions can be communicated with a remote computer 1360 through communication connections 1355 (e.g., wired, wireless, etc.) if desired.

Figure 14A:
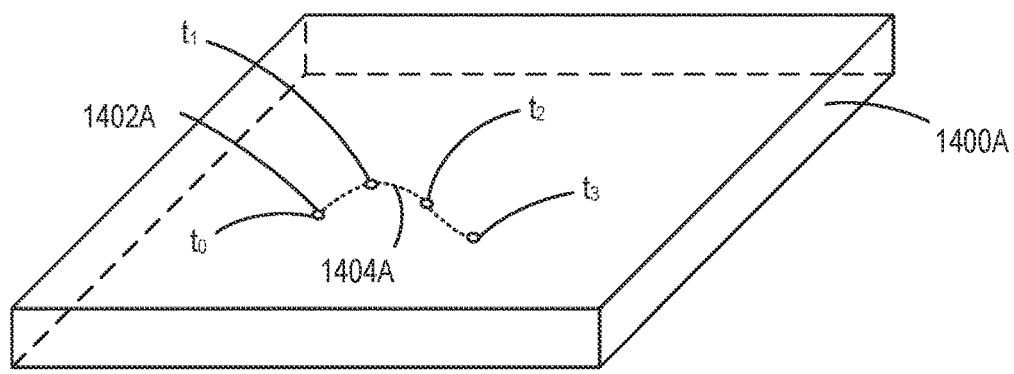
FIGS. 14A-14C are perspective schematics of example sample volumes undergoing growth and detection with holography methods herein.
Figure 14B:
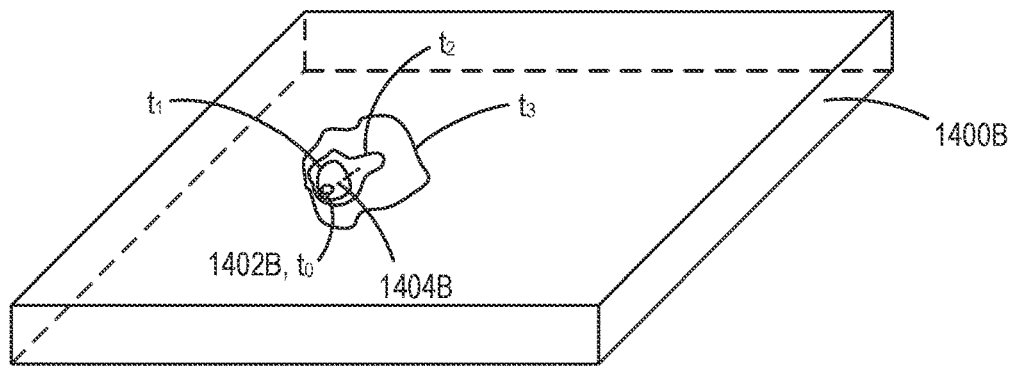
Figure 14C:
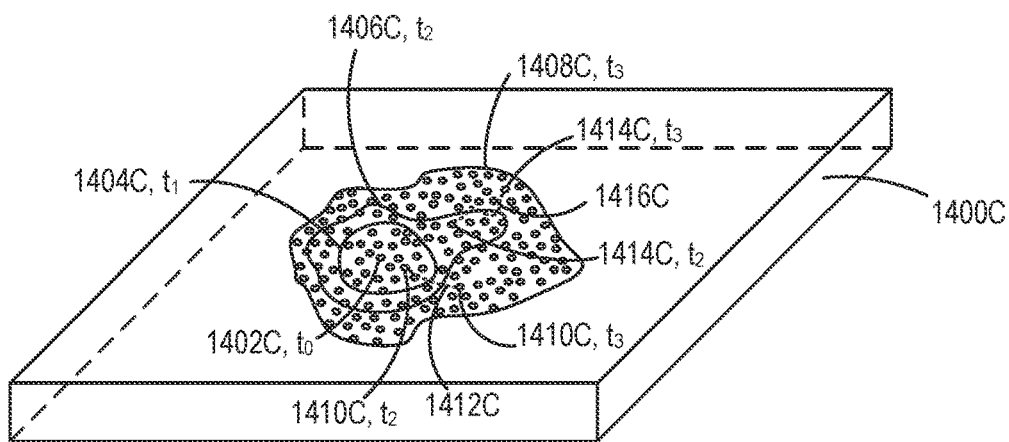

FIGS. 14A-14C are sample volumes 1400A-1400C with contents that can be detected over time through generation and detection of in-line holograms with a holographic apparatus. In sample volume 1400A, an object 1402A is detected at a time to, which can correspond to an initiation of an incubation and test of the sample volume 1400A or a time at a selected point during the test. At a time $t_1$, an object is detected at a different position and the holographic apparatus can determine that the object is associated with the object 1402A, such as through a movement to the new position. Different detected characteristics can be associated with the movement, such as the lack of, or change in the characteristics of (e.g., image variation corresponding to a flagellation or movement wake), the object at the position detected at time to. The object 1402A can be detected at subsequent times $t_2$ and $t_3$ and an object track 1404A can be formed. As shown in FIGS. 14A-14C, the various object tracks and morphological characteristics can be detected in one, two, and/or three spatial dimensions.

The sample volume 1400B shows a growth of an object 1402B in a motile or immobilizing support media. For example, at a time to the object 1402B can be detected. At subsequent times $t_1$-$t_3$, a growth is detected such as through the change in position of an object boundary that corresponds to an area enlargement associated with the object 1402B. An object track 1404B can also be identified, e.g., based on centroid calculations or morphological characteristics of the object 1402B (e.g., color, opacity, shape, size, etc.). In the sample volume 1400C, an object 1402C is detected at a time to with no other objects detected in the surrounding volume, or with some objects detected that can be later subtracted as not corresponding to growing microorganisms. At a time $t_1$, multiple objects are detected surrounding the object 1402C defining a growing object boundary 1404C (e.g., with no objects detected outside the object boundary 1404C). In some examples, each individual object can be detected and movement can be tracked. At later times $t_2$-$t_3$, additional objects are detected indicative of growth of the initial object 1402C and defining respective growing population boundaries 1406C, 1408C. An object 1410C detected at time $t_1$ can be associated with a movement along a track 1412C to a new position at time $t_2$. Another object 1414C detected at time $t_2$ can be associated with a movement along a track 1416C to a new position at time $t_3$. Track characteristics, including directional changes, can be determined based on additional holograms between selected time intervals, debris and/or wake detection, and morphological characteristics including associations between size or shape and movement speed/distance.

Figure 15:
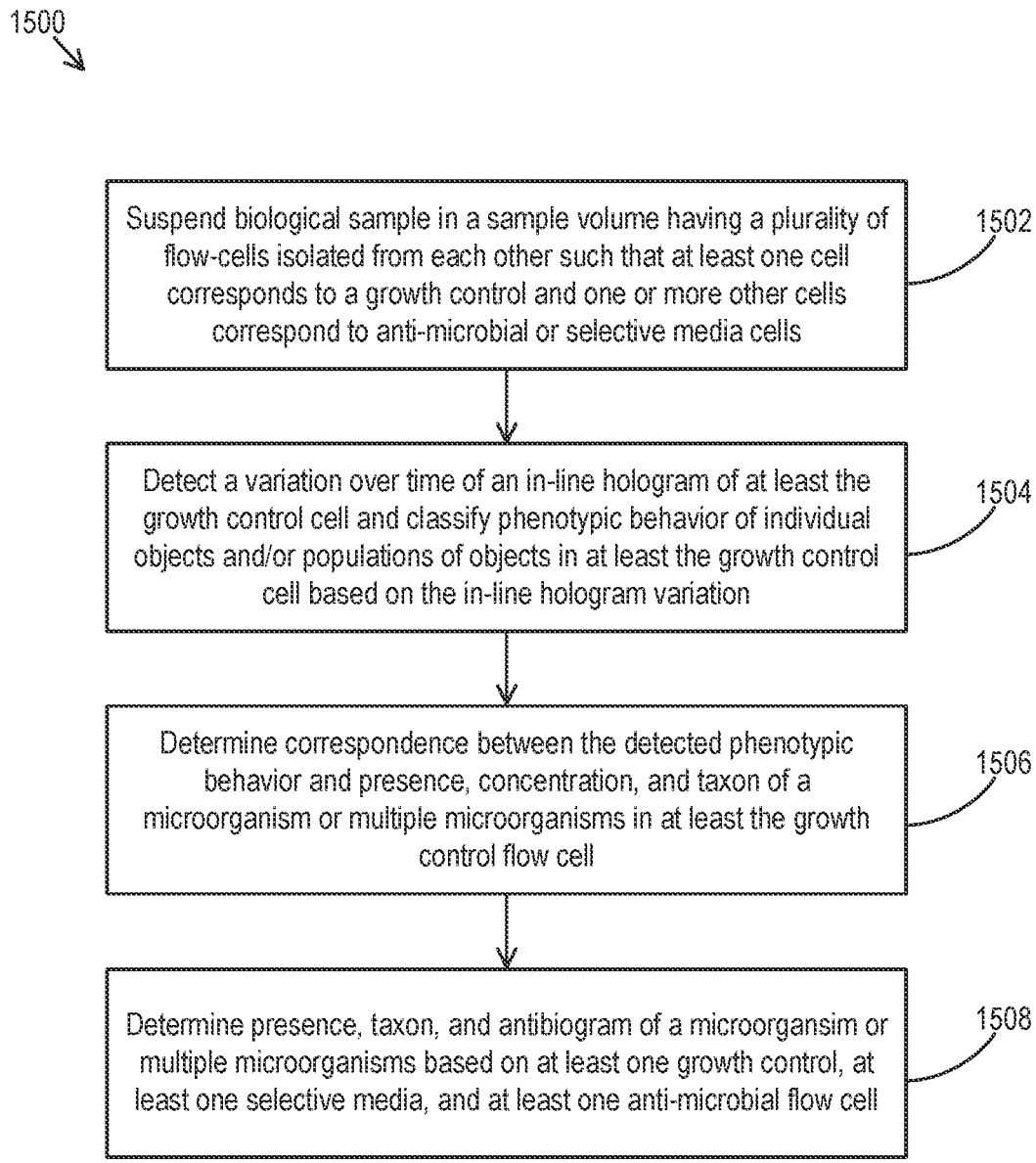
FIG. 15 is a flowchart of another example holography method.

FIG. 15 is an example multiplexed method 1500 of testing biological samples. At 1502, a biological sample is suspended in a sample volume having a plurality of flow-cells isolated from each other such that at least one cell corresponds to a growth control and one or more other cells correspond to anti-microbial or selective media cells. At 1504, a variation over time is detected in multiple in-line holograms of at least the growth control cell and phenotypic behavior of individual objects and/or populations of objects in at least the growth control cell is classified based on the detected hologram variation. At 1506, a correspondence is determined between the detected phenotypic behavior and a presence, concentration, and taxon of a microorganism or multiple microorganisms in at least the growth control flow cell. At 1508, a presence, taxon, and antibiogram of a microorganism or multiple microorganisms is determined based on at least one growth control, at least one selective media, and at least one anti-microbial flow cell.

Figure 16:
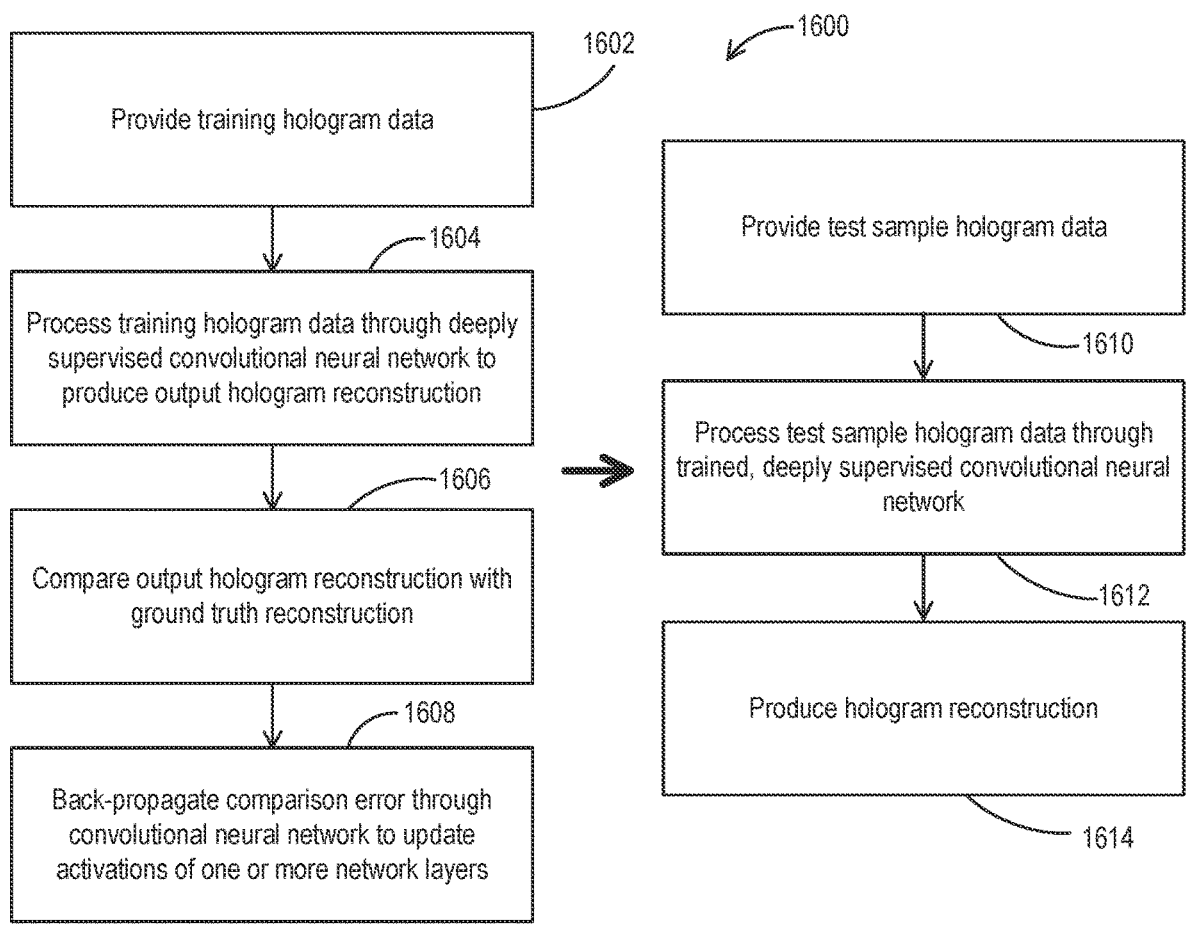
FIGS. 16-17 are flowcharts of example convolutional neural network training and trained testing.

FIG. 16 is an example hologram reconstruction framework 1600 with a convolutional neural network. The hologram reconstruction framework 1600 typically includes a training phase 1602-1608 that refines the parameters of the convolutional neural network. At 1602, a set of hologram training data is provided to a deeply supervised multi-layer convolutional neural network. Training data typically includes a set of holographic data having a known ground truth amplitude/phase spatial reconstruction for a sample volume. At 1604, the training hologram data is processed through the deeply supervised convolutional neural network to produce a reconstruction of the sample volume based on the input training hologram data. At 1606, the output hologram-based reconstruction is compared with the ground truth representation of the sample volume, and at 1608, based on the detected errors, the non-linear activations (e.g., softplus, ReLU, etc.) of one or more network layers of the convolutional neural network are updated by back-propagating comparison error through the convolutional neural network, e.g., via gradient descent. A testing phase 1610-1614 is used on field samples after the convolutional neural network is sufficiently trained. At 1610, data corresponding to an in-line holographic image of a biological test sample volume is provided from an imaging detector and/or memory/storage. At 1612, the data is processed through the trained deeply supervised convolutional neural network, and at 1614 a reconstruction of the sample volume based on the hologram data is produced.

Figure 17:
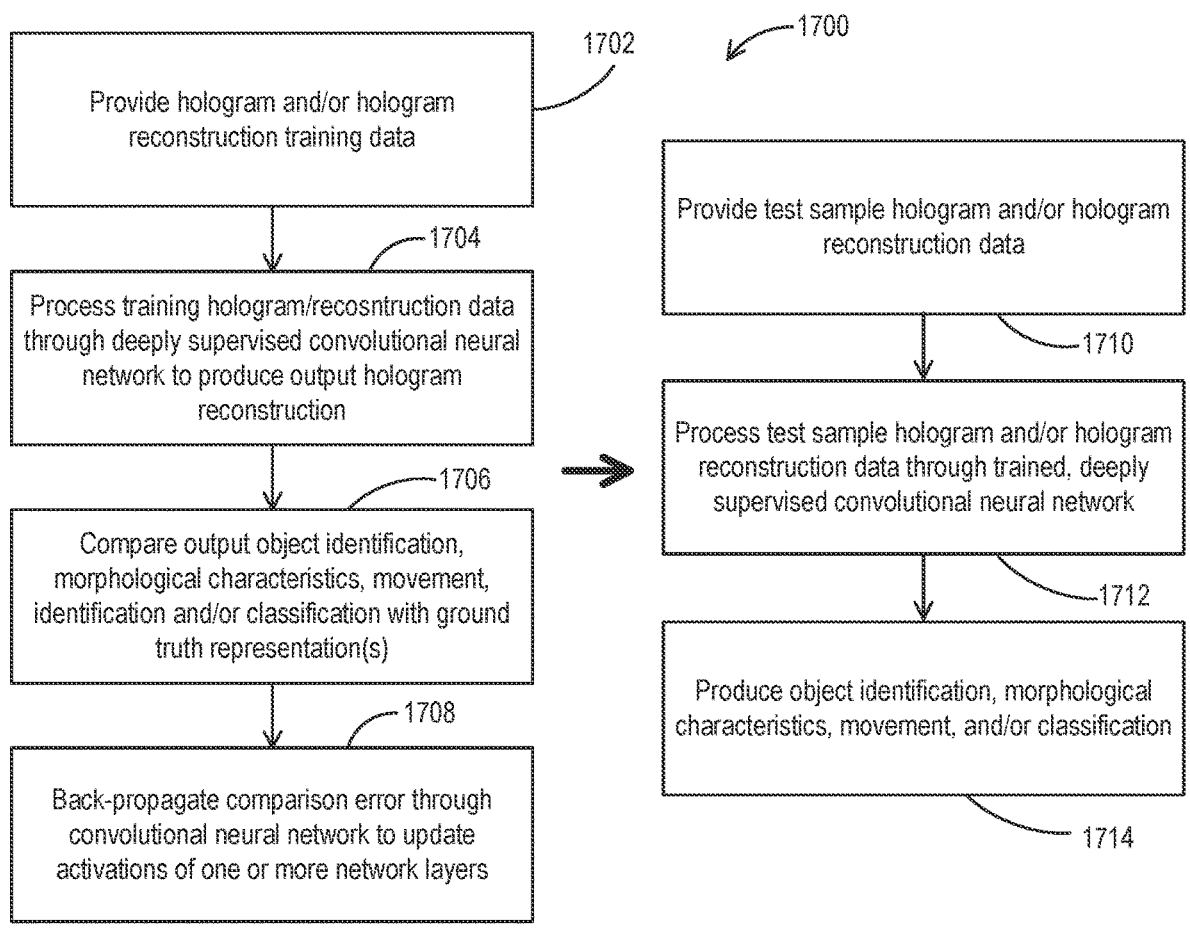

FIG. 17 is an example micro-object identification/classification framework 1700 with a convolutional neural network. The micro-object identification/classification framework 1700 typically includes a training phase 1702-1708 that refines the parameters of the convolutional neural network to converge on an improved output accuracy as additional training data sets are processed. At 1702, a set of hologram training data is provided to a deeply supervised multi-layer convolutional neural network. Training data typically includes a set of hologram data and/or hologram reconstruction data having a known ground truth object identification and/or object classification correspondence for a sample volume that includes various objects. At 1704, the training data is processed through the deeply supervised multi-layer convolutional neural network to produce an output object identification and/or object classification, such as an identification of objects, object morphologies, object movements, and phenotypic classifications. At 1706, output identification and/or classification is compared to the ground truth associated with the training data. At 1708, activations of one or more network layers are updated by back-propagation (e.g., through gradient descent) of the comparison error through the convolutional neural network. A testing phase 1710-1714 can be used on field samples after the convolutional neural network is sufficiently trained. At 1710, data corresponding to an in-line holographic image or reconstructed 3D spatial image of a biological test sample volume is provided. At 1712, the data are processed through the trained deeply supervised convolutional neural network, and at 1714 an object identification and/or classification is produced based on the hologram or reconstruction data.

In view of the many possible embodiments to which the principles of the disclosure may be applied, it should be recognized that the illustrated embodiments are only examples and should not be taken as limiting the scope of the disclosed technology. Rather, the scope of the disclosed technology is defined by the following claims. We therefore claim all that comes within the scope of these claims.

What is claimed is:

1. An in-line holographic system comprising:
   a. an illumination source;
   b. a sample receptacle below the illumination source;
   c. an optical sensor below the sample receptacle; and
   d. a hologram controller coupled to the optical sensor.
2. The system of claim 1, wherein the illumination source is a single illumination source.
3. The system of claim 1, wherein the illumination source comprises more than one illumination source.
4. The system of claim 1, wherein the illumination source is a reference beam source and the reference beam source comprises a lens-free pinhole aperture.
5. The system of claim 1, wherein the illumination source is a reference beam source and the reference beam source comprises a plurality of spaced apart pinhole apertures and the illumination source comprises a plurality of illumination sources.
6. The system of claim 5, wherein the plurality of illumination sources is coupled to the plurality of spaced apart pinhole apertures.
7. The system of claim 1, wherein the illumination source is a reference beam source and the reference beam source comprises a pinhole aperture and the pinhole aperture is coupled to a wavelength filter.
8. The system of claim 1, wherein the system produces an in-line hologram.
9. The system of claim 1, wherein the hologram controller comprises a detector control in communication with the optical sensor or an illumination control in communication with the optical sensor.
10. The system of claim 1, wherein the hologram controller comprises a detector control and an illumination control in communication with the optical sensor.
11. The system of claim 1, wherein the sample receptacle receives a sample container and a portion of the sample container forms at least a part of the sample receptacle.

* * * * *

UNITED STATES PATENT AND TRADEMARK OFFICE
CERTIFICATE OF CORRECTION

PATENT NO. : 11,940,757 B2
APPLICATION NO. : 17/353943
DATED : March 26, 2024
INVENTOR(S) : Oleg Gusyatin It is certified that error appears in the above-identified patent and that said Letters Patent is hereby corrected as shown below:

In the Drawings

FIG. 17, #1704, "recosntruction" should be --reconstruction--.

In the Specification

Column 7, Line 29, "includes" should be --include--.

Column 10, Line 52, "affect" should be --effect--.

Column 12, Line 23, "such as," should be --such as--.

Column 15, Line 42, "is compared" should be --as compared--.

Column 17, Lines 22-23, "about CFU/mL," should be --about 90 CFU/mL,--.

Column 17, Line 30, "about CFU/mL," should be --about 90 CFU/mL,--.

Column 17, Line 64, "example," should be --examples,--.

Column 18, Line 60, "may be require" should be --may require--.

Column 19, Line 31, "is compared" should be --as compared--.

Column 19, Line 35, "example," should be --examples,--.

Column 20, Line 50, "is compared" should be --as compared--.

Column 27, Line 30, "includes" should be --include--.

Signed and Sealed this
Twenty-fifth Day of June, 2024

Katherine Kelly Vidal
*Director of the United States Patent and Trademark Office*

CERTIFICATE OF CORRECTION (continued)
U.S. Pat. No. 11,940,757 B2

Column 28, Line 55, "connections 650 to communicate with external device" should be --connection 650 to communicate with an external device--.

Column 29, Line 55, "have" should be --having--.

Column 32, Line 8, "is" should be --are--.

Column 33, Line 55, "testing a sample" should be --testing of a sample--.

Column 35, Lines 60-61, "in the form computer-executable instructions" should be --in the form of computer-executable instructions--.

Column 37, Line 35, "to," should be --$t_0$,--.

Column 37, Line 45, "to." should be --$t_0$.--.

Column 37, Line 52, "to" should be --$t_0$--.

Column 37, Line 60, "to" should be --$t_0$--.